(12) United States Patent
Lin

(10) Patent No.: US 9,364,543 B2
(45) Date of Patent: Jun. 14, 2016

(54) VISIBLE LIGHT CURABLE HYDROGELS AND METHODS FOR USING

(71) Applicant: Indiana University Research and Technology Corporation, Indianapolis, IN (US)

(72) Inventor: Chien-Chi Lin, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/062,296

(22) Filed: Oct. 24, 2013

(65) Prior Publication Data

US 2014/0112960 A1    Apr. 24, 2014

Related U.S. Application Data

(60) Provisional application No. 61/717,687, filed on Oct. 24, 2012.

(51) Int. Cl.
*A61K 47/34* (2006.01)
*A61K 51/12* (2006.01)
*C08G 18/83* (2006.01)

(52) U.S. Cl.
CPC ............ *A61K 47/34* (2013.01); *A61K 51/1213* (2013.01); *C08G 18/835* (2013.01)

(58) Field of Classification Search
CPC ... A61K 47/34; A61K 51/1213; C08G 18/835
See application file for complete search history.

(56) References Cited

FOREIGN PATENT DOCUMENTS

WO    WO 2010017264 A2 *   2/2010

OTHER PUBLICATIONS

Fairbanks et al., Adv. Mater., 2009, 21, 5005-5010.*
Ortiz et al., Carbohydrate Polymers, 2010, 82, 822-828.*
Gotro, http://polymerinnovationblog.com/uv-curing-part-three-free-radical-photoinitiators/, Jan. 2016, obtained online on Mar. 18, 2016.*
Han Shih, Chien-Chi Lin, Macromol. Rapid Commun. 2013, 34, 269-273.
Lin, et al. Functional PEG-peptide hydrogels to modulate local inflammation induced by the pro-inflammatory cytokine TNFa. Biomaterials. 2009(30):4907-4914.
Lin, et al. Regulating MCP-1 diffusion in affinity hydrogels for enhancing immuno-isolation. J. Control, Release. 2010 (142):384-391.
Anderson, et al. The performance of human mesenchymal stem cells encapsulated in cell-degradable polymer-peptide hydrogels. Biomaterials. 2011(32):3564-3574.
Lin, et al. Cell-cell communication mimicry with PEG hydrogels for enhancing β-cell function. Proceedings of the National Academy of Sciences USA. 2011(108):6380-6385.
Lin et al Peg hydrogeis formed by thiol-ene photo-click chemistry and their effect on the formation and recovery of insulin-secreting cell spheroids. Biomaterials. 2011(32):9685-9695.
Shih, et al. Cross-linking and degradation of step-growth hydrogeis formed by thiol-ene photoclick chemistry. Biomacromolecules. 2012(13)2003-2012.
Sawhney, et al. Interfacial photopolymerization of poly(ethylene glycol)-based hydrogels upon alginate-poly(I-lysine) microcapsules for enhanced biocompatibility. Biomaterials. 1993 14(13)1008-1016.
Kizilel et al. Modeling of PEG Hydrogel Membranes for Biomedical Applications. Macromol. React. Eng. 2009(3) 271-287.

* cited by examiner

*Primary Examiner* — Abigail Fisher
(74) *Attorney, Agent, or Firm* — Barnes & Thornburg LLP

(57) ABSTRACT

This disclosure provides compositions comprising a visible light-curable mixture capable of forming a biocompatible hydrogel, hydrogels prepared from the hydrogel precursor mixtures, and a biocompatible delivery system comprising a hydrogel. The disclosure also provides a process for preparing a multi layer hydrogel delivery system.

17 Claims, 23 Drawing Sheets

VISIBLE LIGHT CURABLE HYDROGELS AND METHODS FOR USING

CROSS-REFERENCE TO RELATED APPLICATIONS

This application claims the benefit under 35 U.S.C. §119 (e) of U.S. Provisional Application Ser. No. 61/717,687, filed Oct. 24, 2012, the disclosure of which is incorporated herein by reference.

GOVERNMENT RIGHTS

This invention was made with government support under R21EB013717 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 4.0 kilobytes ACII (Text) file named "227067_Sequence_Listing.txt" created on Oct. 23, 2013.

TECHNICAL FIELD

The invention described herein pertains to hydrogels, and compositions for preparing hydrogels.

BACKGROUND AND SUMMARY OF THE INVENTION

Hydrogels prepared from photo-polymerizations have been an attractive class of biomaterials for tissue engineering and regenerative medicine applications. Radical initiated photo-polymerizations have also received significant attention for in situ encapsulation and delivery of biologics, including cells, proteins, RNAs, and DNAs. In general, photo-polymerizations for hydrogel synthesis are initiated by either long wavelength ultraviolet light (e.g., $\lambda=365$ nm) using a type I initiator (e.g., Irgacure 2959 or lithium arylphosphanate), or alternatively using visible light ($\lambda=400$-700 nm) with a type II initiator (e.g., eosin-Y) and appropriate co-initiator/co-monomer. Following light exposure, a type I (cleavage type) photoinitiator readily absorbs photons and decomposes into two primary radicals, which participate in the polymerization process. In contrast, a type II photoinitiator absorbs photons to achieve an excited state, which abstracts a hydrogen atom from a reactant to form a secondary radical, which participates in the polymerization process. UV-mediated reaction is generally a preferred method for preparing hydrogels due to the simplicity in preparing polymer precursor solutions, as well as the rapid and spatial-temporally controlled gelation kinetics. However, visible light-mediated gelation is believed herein to be more desirable for biomedical applications due to the lower potential for light-induced damage.

For example, even at long wavelengths (e.g., $\lambda=365$ nm), the use of UV light for biomedical applications may raise biosafety concerns. Though, conventional visible light-mediated polymerization is more desirable, the utility of conventional visible light-mediated polymerization is limited by its slow reaction kinetics, and the general necessity to add co-monomers and co-initiators, each of which may be cytotoxic. For example, visible light sources ($\lambda=400$ to 700 nm) can be used together with appropriate photoinitiators (e.g., eosin-Y) to initiate photopolymerizations. When eosin-Y is excited by visible light, it abstracts hydrogen atoms from a co-initiator triethanolamine (TEOA) to form secondary radicals. These radicals then propagate through vinyl groups on the macromers (e.g., poly(ethylene glycol) diacrylate or PEGDA) to form a crosslinked polymer network. Unfortunately, the photopolymerization kinetics using eosin-Y and TEOA are slow and therefore a co-monomer, such as 1-vinyl-2 pyrrolidinone (NVP) is commonly added to accelerate the gelation kinetics. These additional components (TEOA and NVP) make adjusting the compositions of precursor solution more complicated. In addition, the use of co-monomers may be unaccompanied by undesirable cytotoxicity.

Further, two general criteria, namely solubility in water and molar absorptivity at cytocompatible wavelengths ($\lambda=360$ nm), are used to evaluate the suitability of a photoinitiator in biomedical applications. Thus, only a few photoinitiators have been reported to fulfill these criteria and are considered cytocompatible to be used in preparing hydrogels for in situ cell encapsulation. Those photoinitiators include type I initiators, such as Irgacure-2959 (I-2959) and lithium arylphosphinate (LAP), and type II initiators, such as eosin-Y (a fluorescent red dye for histological staining). Commercially available I-2959 has low water solubility (<0.5 wt %) and low molar absorptivity at 365 nm ($\epsilon<10$ M$^{-1}$ cm$^{-1}$). Furthermore, I-2959 cannot be used in visible light-mediated photocrosslinking systems due to its near zero molar absorptivity at wavelengths higher than 400 nm. Even though LAP is highly water-soluble (>5 wt %) and has higher molar absorptivity at 365 nm ($\epsilon\sim200$ M$^{-1}$ cm$^{-1}$), its utility in visible light range is also limited ($\epsilon\sim30$ M$^{-1}$ cm$^{-1}$ at 405 nm). In contrast, type II photoinitiators, such as eosin-derivatives, are highly water-soluble and can be readily excited by visible light ($\lambda=400$ to 700 nm). Although eosin-Y itself is not cytotoxic, the use of eosin-Y is hampered by the need to include one or more toxic co-initiators and accelerants to generate sufficient radicals to achieve high functional group conversion and yield stable crosslinked hydrogels.

Accordingly, there is a need for new compositions for preparing hydrogels using visible light-mediated polymerization without the need to add cytotoxic co-monomers.

It has been discovered that the hydrogel precursor mixtures described herein undergo rapid visible light-mediated polymerization, also termed gelation herein, and are useful for preparing cytocompatible thiol-ene photo-click hydrogels. The hydrogel precursor mixtures include cytocompatible visible light photoinitiators, such as eosin-Y (EY), and do not require adding any cytotoxic components to achieve rapid gelation under ambient conditions. It has also been discovered herein that multi-layered thiol-ene hydrogels can be fabricated using a surface-mediated thiol-ene photopolymerization. It has also been discovered herein that such multi-layered thiol-ene hydrogels may be prepared by manipulating the diffusion rate of the initiator, such as eosin-Y.

In one illustrative embodiment of the invention, hydrogel precursor mixtures capable of forming a hydrogel are described herein. In one aspect, the mixtures include one or more macromers, each comprising a carbon-carbon multiple bond, one or more crosslinking agents, and a type II photoinitiator having at least one peak absorbance in the visible light region.

In another embodiment, hydrogels are described herein that are prepared from the hydrogel precursor mixtures described herein.

In another embodiment, hydrogel delivery systems are described herein. In another embodiment, hydrogel delivery systems are described herein that comprise a single hydrogel layer. In another embodiment, hydrogel delivery systems are described herein that comprise two or more hydrogel layers. In one variation, each layer of the multiple layer hydrogels have the same or a similar composition, In another variation, two or more have a different composition from each other. The hydrogel delivery systems may include one or more populations of cells, one or more therapeutic agents, one or more diagnostic agents, or any combination of the foregoing.

It is appreciated herein that the delivery systems described herein may be used alone or in combination with other compounds useful for treating or diagnosing diseases.

DETAILED DESCRIPTION

Hydrogels described herein are generally formed under radical polymerization conditions. Illustratively, Type II initiators are activated with light in the visual spectrum and extract hydrogen atoms from reactive thiol groups as follows:

The formed radical (R—S). reacts with a carbon-carbon multiple bond, such as a norbornene as follows:

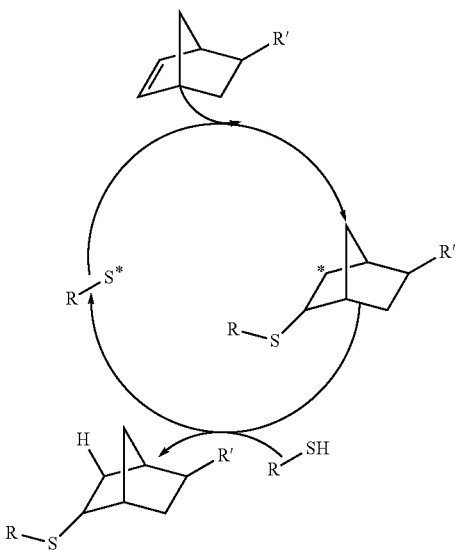

Figure 1:
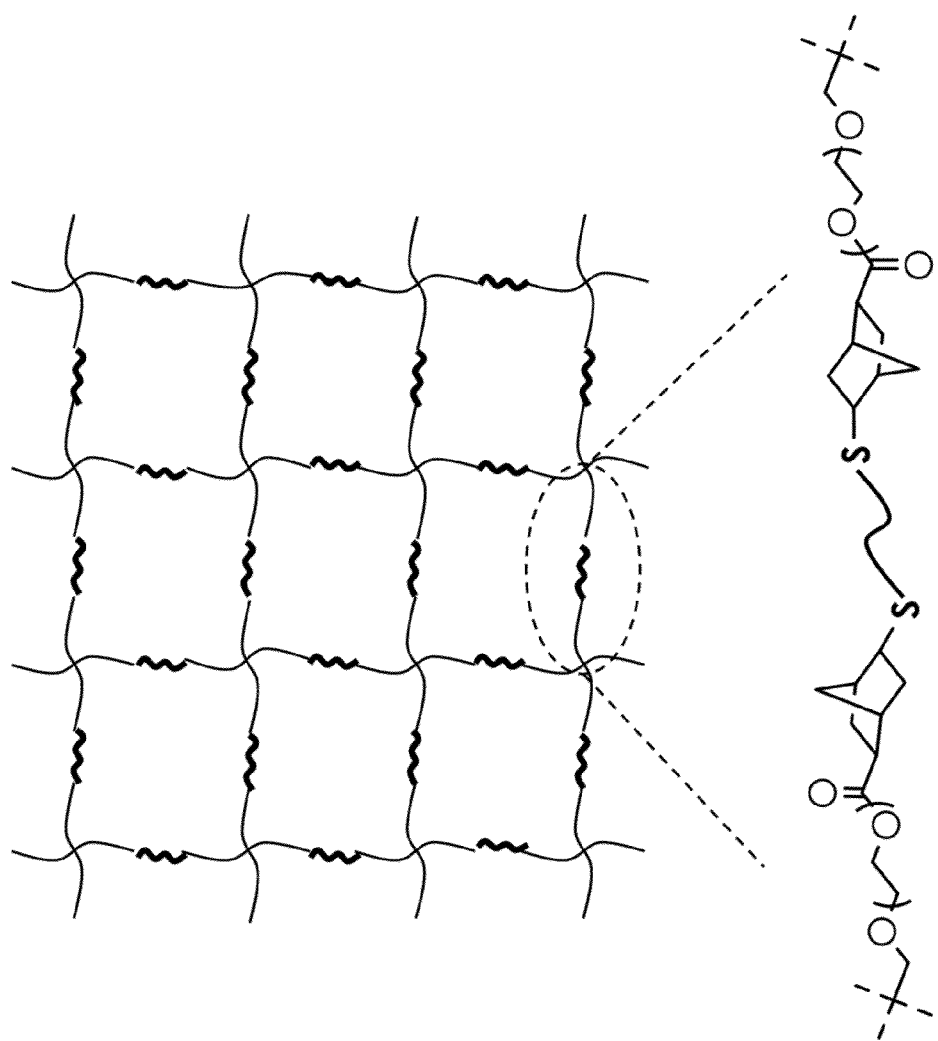
FIG. 1 shows an illustrative repeating matrix arrangement of the hydrogel structure, and further illustrated by a dithiol cross-linked PEG4NB.

In another embodiment, the hydrogels described herein are formed by step-growth polymerization rather than chain-growth polymerization. Without being bound by theory, it is believed herein that certain improved properties exhibited by hydrogels described herein may be enhanced at least in part by using the step-growth process. Step-growth polymerization reportedly provides a more organized and/or more regularly repeating pattern, structure, or matrix, than equivalent chain-growth polymerization. In another embodiment, at least a portion of the hydrogel structure described herein may include a repeating matrix such as shown in FIG. 1.

Several illustrative embodiments of the invention are described by the following enumerated clauses:

1. A composition comprising a visible light-curable mixture capable of forming a biocompatible hydrogel, the mixture comprising one or more macromers, each comprising a carbon-carbon multiple bond, one or more cross-linking agents, and one or more type II photoinitiators, each having at least one peak absorbance in the visible light range.

2a. The composition of the preceding clause wherein the peak absorbance is in the range from about 400 to about 700 nm.

2b. The composition of any one of the preceding clauses wherein the peak absorbance is in the range from about 450 to about 560 nm.

3a. The composition of any one of the preceding clauses wherein the peak absorbance is in the range from about 500 to about 530 nm. It is appreciated that eosins have peak absorbance in this range.

3b. The composition of any one of the preceding clauses wherein the peak absorbance is in the range from about 515 to about 525 nm.

3c. The composition of any one of the preceding clauses wherein the peak absorbance is about 515 nm.

3d. The composition of any one of the preceding clauses wherein the peak absorbance is in the range from about 420 to about 480 nm. It is appreciated that riboflavins and certain coumarins, such as 4-hydroxycoumarins, have peak absorbance in this range.

3e. The composition of any one of the preceding clauses wherein the peak absorbance is in the range from about 400 to about 420 nm. It is appreciated that coumarin has a strong absorbance in this range.

3f. The composition of any one of the preceding clauses wherein the peak absorbance is about 400 nm.

3g. The composition of any one of the preceding clauses wherein the peak absorbance is in the range from about 550 to about 570 nm. It is appreciated that Rose Bengal has peak absorbance in this range.

3h. The composition of any one of the preceding clauses wherein the peak absorbance is about 560 nm.

4. The composition of any one of the preceding clauses wherein the mixture is substantially free of or free of co-initiators, including cytotoxic co-initiators, such as co-initiators included in conventional hydrogels to increase the reaction kinetics.

5. The composition of any one of the preceding clauses wherein the mixture is substantially free of or free of co-monomers, including cytotoxic co-monomers, such as co-monomers included in conventional hydrogels to decrease gelation time and/or gel point.

6a. The composition of any one of the preceding clauses wherein the mixture has a rapid gel point.

6b. The composition of any one of the preceding clauses wherein the mixture has a gel point that is about 25% or more faster than a conventional hydrogel mixture prepared under comparable conditions of time, wavelength, and light intensity, such as a broad spectrum white light source of about 70,000 Lux.

6c. The composition of any one of the preceding clauses wherein the mixture has a gel point that is about 33% or more faster than a conventional hydrogel mixture prepared under comparable conditions of time, wavelength, and light intensity, such as a broad spectrum white light source of about 70,000 Lux.

6d. The composition of any one of the preceding clauses wherein the mixture has a gel point that is about 50% or more faster than a conventional hydrogel mixture prepared under comparable conditions of time, wavelength, and light intensity, such as a broad spectrum white light source of about 70,000 Lux.

7a. The composition of any one of the preceding clauses wherein the mixture has a rapid complete gelation time.

7b. The composition of any one of the preceding clauses wherein the mixture has a complete gelation time that is about 25% or more shorter than a conventional hydrogel mixture prepared under comparable conditions of time, wavelength, and light intensity, such as a broad spectrum white light source of about 70,000 Lux.

7c. The composition of any one of the preceding clauses wherein the mixture has a complete gelation time that is about 33% or more shorter than a conventional hydrogel mixture prepared under comparable conditions of time, wavelength, and light intensity, such as a broad spectrum white light source of about 70,000 Lux.

7d. The composition of any one of the preceding clauses wherein the mixture has a complete gelation time that is about 50% or more shorter than a conventional hydrogel mixture prepared under comparable conditions of time, wavelength, and light intensity, such as a broad spectrum white light source of about 70,000 Lux.

8a. The composition of any one of the preceding clauses wherein the biocompatible hydrogel exhibits low gel shear modulus.

8b. The composition of any one of the preceding clauses wherein the biocompatible hydrogel exhibits a gel shear modulus of about 10,000 or less, or alternatively of about 5,000 Pa or less.

9a. The composition of any one of the preceding clauses wherein the biocompatible hydrogel exhibits high gel elastic modulus, such as a high gel elastic modulus indicative of high cross-linking.

10a. The composition of any one of the preceding clauses wherein the mixture further comprises a therapeutic agent, a diagnostic agent, or a combination thereof.

10b. The composition of any one of the preceding clauses wherein the biocompatible hydrogel is capable of use for encapsulation and delivery of a therapeutic agent, a diagnostic agent, or a combination thereof.

10c. The composition of any one of the preceding clauses wherein the mixture further comprises a protein or nucleic acid, or a combination thereof.

10d. The composition of any one of the preceding clauses wherein the biocompatible hydrogel is capable of use for encapsulation and delivery of a protein or nucleic acid, or a combination thereof.

10e. The composition of any one of the preceding clauses wherein the mixture further comprises an immunologic agent.

10f. The composition of any one of the preceding clauses wherein the biocompatible hydrogel is capable of use for encapsulation and delivery of an immunologic agent.

11a. The composition of any one of the preceding clauses wherein the mixture further comprises a population of cells.

11b. The composition of any one of the preceding clauses wherein the biocompatible hydrogel is capable of use for encapsulation and delivery of a population of cells.

11c. The composition of any one of the preceding clauses wherein the cells are human mesenchymal stem cells (hMSCs).

11d. The composition of any one of the preceding clauses wherein the cells are human mouse insulinoma (MIN6) β-cells.

11e. The composition of any one of the preceding clauses wherein the cells are hepatocytes.

12. The composition of any one of the preceding clauses wherein the biocompatible hydrogel is capable of forming a conformal gel coating for immuno-isolation of cells.

13. The composition of any one of the preceding clauses wherein the cells are isolated islets.

14. The composition of any one of the preceding clauses wherein the cells are coated with a dithiol.

15. The composition of any one of the preceding clauses wherein the dithiol is a PEG dithiol.

16a. The composition of any one of the preceding clauses wherein the photoinitiator is selected from the group consisting of eosins, Rose Bengal, riboflavins, coumarin, and 4-hydroxycoumarin, and combinations thereof.

16b. The composition of any one of the preceding clauses wherein the photoinitiator is eosin Y or eosin B.

16c. The composition of any one of the preceding clauses wherein the photoinitiator is eosin Y.

16d. The composition of any one of the preceding clauses wherein the photoinitiator is Rose Bengal.

16e. The composition of any one of the preceding clauses wherein the photoinitiator is water soluble.

17a. The composition of any one of the preceding clauses wherein the cross-linking agent is a polythiol compound.

17b. The composition of any one of the preceding clauses wherein the cross-linking agent is a bis-cysteine peptide, such as peptides of the sequence C—(X)$_n$—C, where X is an amino acid or peptide, and n is an integer from 1 to 15, or alternatively 1 to 10.

17c. The composition of any one of the preceding clauses wherein the bis-cysteine peptide is a chymotrypsin sensitive peptide, such as but not limited to CGGYC (SEQ ID NO:1), Matrix metalloproteinase sensitive peptide, such as but not limited to CGPQGIWGQC (SEQ ID NO:2), or a mixture thereof. It is appreciated that using such bis-cysteine peptide cross-linking agents may be advantageous by allowing for biodegradation via more specific cellular processes.

17d. The composition of any one of the preceding clauses wherein the crosslinking agent is a PEG dithiol.

17e. The composition of any one of the preceding clauses wherein the PEG dithiol is of the formula

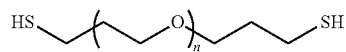

where n is in the range from about 20 to about 1000.

17f. The composition of any one of the preceding clauses wherein the PEG dithiol is of the formula

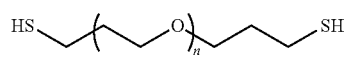

where n is in the range from about 40 to about 1000.

17g. The composition of any one of the preceding clauses wherein the PEG dithiol is of the formula

where n is in the range from about 40 to about 400.

17h. The composition of any one of the preceding clauses wherein the crosslinking agent is dithiothreitol (DTT).

18a. The composition of any one of the preceding clauses wherein the carbon-carbon multiple bond is an alkenyl group.

18b. The composition of any one of the preceding clauses wherein the carbon-carbon multiple bond is a vinyl group.

19. The composition of any one of the preceding clauses wherein the carbon-carbon multiple bond is substantially non-polar or non-polar.

20. The composition of any one of the preceding clauses wherein the carbon-carbon multiple bond is a strained alkenyl group.

21a. The composition of any one of the preceding clauses wherein the carbon-carbon multiple bond is contained in a cyclic structure.

21b. The composition of any one of the preceding clauses wherein the carbon-carbon multiple bond is contained in a norbornenyl group.

22a. The composition of any one of the preceding clauses wherein the macromer comprises one or more polyhydroxy groups.

22b. The composition of any one of the preceding clauses wherein the polyhydroxy groups are poly(alkylene glycol) groups.

22c. The composition of any one of the preceding clauses wherein the polyhydroxy groups are poly(ethylene glycol) groups.

23. The composition of any one of the preceding clauses wherein the macromer comprises a polyvalent radical having at least three valences, where each valence is attached to a linker attached to the carbon-carbon multiple bond.

24a. The composition of any one of the preceding clauses wherein the polyvalent radical is a branched core polyradical.

24b. The composition of any one of the preceding clauses wherein the macromer comprises a polyvalent radical have four or more arms.

24c. The composition of any one of the preceding clauses wherein the macromer comprises a polyvalent radical have five or more arms.

24d. The composition of any one of the preceding clauses wherein the macromer comprises a polyvalent radical have six or more arms.

24e. The composition of any one of the preceding clauses wherein the polyvalent radical is selected from the group consisting of tetramethylol propane (TMP), pentaerythritol (PE), tetramethylol propane pentaerythritol ether, and dipentaerythritol (DPE).

25a. The composition of any one of the preceding clauses wherein the polyvalent radical is a linear polyradical.

25b. The composition of any one of the preceding clauses wherein the linear polyradical is a polyvinyl alcohol.

25c. The composition of any one of the preceding clauses wherein the linear polyradical is a polyglycerol.

26a. The composition of any one of the preceding clauses wherein the linker attached to the carbon-carbon multiple bond is a poly(ethylene glycol)-norbornenyl ester.

26b. The composition of any one of the preceding clauses wherein the macromer is a pentaeyrthritol tetra(poly(ethylene glycol)-norbornenyl ester) (PEG4NB).

27a. The composition of any one of the preceding clauses wherein the linker attached to the carbon-carbon multiple bond is a poly(ethylene glycol)-norbornenyl amide.

27b. The composition of any one of the preceding clauses wherein the macromer is a pentaeyrthritol tetra(poly(ethylene glycol)-norbornenyl amide) (PEG4aNB).

28a. The composition of any one of the preceding clauses wherein the PEG has a molecular weight in the range from about 5,000 to about 40,000.

28b. The composition of any one of the preceding clauses wherein the PEG has a molecular weight in the range from about 5,000 to about 20,000.

29. The composition of any one of the preceding clauses wherein the linker attached to the carbon-carbon multiple bond is a poly(vinyl alcohol)-norbornenyl ester.

30. The composition of any one of the preceding clauses wherein the linker attached to the carbon-carbon multiple bond is a poly(vinyl alcohol)-norbornenyl amide.

31a. The composition of any one of the preceding clauses wherein the mixture comprises about 2 wt % or greater of macromer.

31b. The composition of any one of the preceding clauses wherein the mixture comprises about 5 wt % or greater of macromer.

31c. The composition of any one of the preceding clauses wherein the mixture comprises about 2 wt % to about 30 wt % of macromer.

31d. The composition of any one of the preceding clauses wherein the mixture comprises about 5 wt % to about 30 wt % of macromer.

31e. The composition of any one of the preceding clauses wherein the mixture comprises about 5 wt % to about 20 wt % of macromer.

32a. The composition of any one of the preceding clauses wherein the mixture comprises about 2 mM or less initiator.

32b. The composition of any one of the preceding clauses wherein the mixture comprises about 2 mM to about 0.1 mM initiator.

32c. The composition of any one of the preceding clauses wherein the mixture comprises about 0.5 mM to about 0.1 mM.

33a. The composition of any one of the preceding clauses wherein the mixture comprises a ratio of crosslinking agent to macromer carbon-carbon unsaturated bond in the range from about 1.5:1 to about 1:0.4.

33b. The composition of any one of the preceding clauses wherein the mixture comprises a ratio of crosslinking agent to macromer carbon-carbon unsaturated bond in the range from about 1.5:1 to about 1:0.5.

33c. The composition of any one of the preceding clauses wherein the mixture comprises a ratio of crosslinking agent to macromer carbon-carbon unsaturated bond in the range from about 1.5:1 to about 1:0.6.

33d. The composition of any one of the preceding clauses wherein the mixture comprises a ratio of crosslinking agent to macromer carbon-carbon unsaturated bond in the range from about 1.5:1 to about 1:0.7.

33e. The composition of any one of the preceding clauses wherein the mixture comprises a ratio of crosslinking agent to macromer carbon-carbon unsaturated bond in the range from about 1.5:1 to about 1:0.8.

33f. The composition of any one of the preceding clauses wherein the mixture comprises a ratio of crosslinking agent to macromer carbon-carbon unsaturated bond in the range from about 1.5:1 to about 1:0.9.

33g. The composition of any one of the preceding clauses wherein the mixture comprises a ratio of crosslinking agent to macromer carbon-carbon unsaturated bond in the range from about 1.5:1 to about 1:0.95.

33h. The composition of any one of the preceding clauses wherein the mixture comprises a ratio of crosslinking agent to macromer carbon-carbon unsaturated bond in the range from about 1.5:1 to about 1:1.

34a. The composition of any one of the preceding clauses wherein the mixture comprises a ratio of crosslinking agent to macromer carbon-carbon unsaturated bond in the range from about 1:1 to about 1:0.4.

34b. The composition of any one of the preceding clauses wherein the mixture comprises a ratio of crosslinking agent to macromer carbon-carbon unsaturated bond in the range from about 1:1 to about 1:0.5.

34c. The composition of any one of the preceding clauses wherein the mixture comprises a ratio of crosslinking agent to macromer carbon-carbon unsaturated bond in the range from about 1:1 to about 1:0.6.

34d. The composition of any one of the preceding clauses wherein the mixture comprises a ratio of crosslinking agent to macromer carbon-carbon unsaturated bond in the range from about 1:1 to about 1:0.7.

34e. The composition of any one of the preceding clauses wherein the mixture comprises a ratio of crosslinking agent to macromer carbon-carbon unsaturated bond in the range from about 1:1 to about 1:0.8.

34f. The composition of any one of the preceding clauses wherein the mixture comprises a ratio of crosslinking agent to macromer carbon-carbon unsaturated bond in the range from about 1:1 to about 1:0.9.

34g. The composition of any one of the preceding clauses wherein the mixture comprises a ratio of crosslinking agent to macromer carbon-carbon unsaturated bond in the range from about 1:1 to about 1:0.95.

34h. The composition of any one of the preceding clauses wherein the mixture comprises a ratio of crosslinking agent to macromer carbon-carbon unsaturated bond of about 1:1.

35. A biocompatible delivery system comprising a hydrogel formed from the precursor mixture of any one of the preceding clauses and coating a biologically active agent.

36. The delivery system of the preceding clause wherein the biologically active agent is a therapeutic agent, a diagnostic agent, or a combination thereof.

37. The delivery system of any one of the preceding clauses wherein the biologically active agent is a protein or nucleic acid.

38. The delivery system of any one of the preceding clauses wherein the biologically active agent is an immunologic agent.

39. The delivery system of any one of the preceding clauses wherein the biologically active agent is a population of cells.

39a. The delivery system of any one of the preceding clauses wherein the cells are human mesenchymal stem cells (hMSCs).

39b. The delivery system of any one of the preceding clauses wherein the cells are human MIN6 β-cells.

39c. The delivery system of any one of the preceding clauses wherein the cells are hepatocytes.

39d. The delivery system of any one of the preceding clauses wherein the cells are isolated islets.

39e. The delivery system of any one of the preceding clauses wherein the cells are coated with a dithiol.

39f. The delivery system of any one of the preceding clauses wherein the dithiol is a PEG dithiol.

40a. The delivery system of any one of the preceding clauses wherein the hydrogel is a two layer hydrogel, each with independently selected characteristics.

40b. The delivery system of any one of the preceding clauses wherein the biocompatible hydrogel is multi-layered, where each layer has independently selected characteristics.

41. A process for preparing a multi layer hydrogel delivery system, the process comprising the steps of
(a) preparing a first hydrogel from a composition according to any one of the preceding clauses;
(b) optionally diffusing away at least a portion of the initiator;
(c) contacting the first hydrogel with a composition comprising one or more macromers, each comprising a carbon-carbon multiple bond, and one or more cross-linking agents according to any one of the preceding clauses; and
(d) exposing the composition to visible light to form a second hydrogel layer on the first hydrogel; and
(e) optionally repeating steps (c) and (d).

42. The process of the preceding clause wherein the first hydrogel and the second hydrogel are chemically substantially the same or chemically the same, and/or have substantially the same or the same mechanical properties and/or characteristics.

43. The process of clause 40 wherein the first hydrogel and the second hydrogel are chemically different or have different mechanical properties or characteristics.

It is to be understood herein that hydrogels that are chemically the same or chemically different may be the same or different, respectively, with reference to chemical composition of the hydrogel itself, and/or with reference to a material encapsulated in the hydrogel, such as a therapeutic agent, a diagnostic agent, or a combination thereof, a protein or nucleic acid, or a combination thereof, an immunologic agent, or a population of cells In another illustrative embodiment, the macromer is a compound of the formula

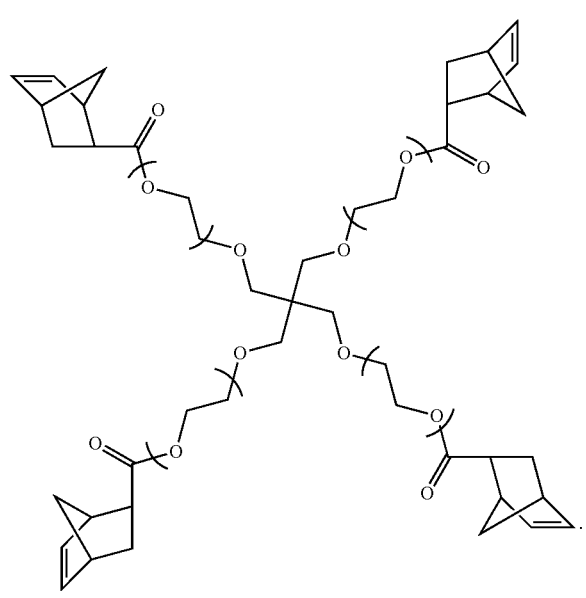

PEG4NB

In another illustrative embodiment, the macromer is a compound of the formula

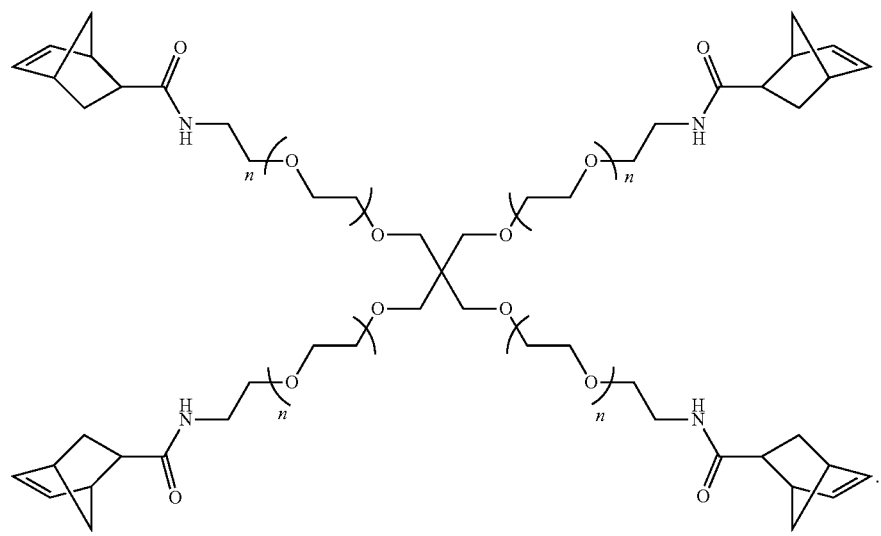

PEG4aNB

Illustratively, the PEG in each of the foregoing embodiments has a molecular weight of about 20 kDa.

Hydrogels preparable from the compositions described herein exhibit a tunable shear modulus. In one variation, hydrogels preparable from the compositions described herein exhibit a low shear modulus. Hydrogels preparable from the compositions described herein exhibit a tunable elastic modulus. In another variation, hydrogels preparable from the compositions described herein exhibit high elastic modulus. Hydrogels preparable from the compositions described herein exhibit a tunable mass swelling ratio. In configurations adapted for cell encapsulation, hydrogels preparable from the compositions described herein exhibit high mass swelling ratio. Without being bound by theory, it is believed herein that high mass swelling ratio is advantageous for encapsulated cells, as a mechanism to increase or provide an adequate supply of water to the cells. In configurations adapted for drug delivery, hydrogels preparable from the compositions described herein exhibit low mass swelling ratio. Without being bound by theory, it is believed herein that low mass swelling ratio is advantageous for controllable delivery of the encapsulated cargo, such as controllable delivery of a therapeutic agent, a diagnostic agent, or a combination thereof, controllable delivery of a protein or nucleic acid, or a combination thereof, controllable delivery of an immunologic agent, or controllable delivery of a population of cells.

In another embodiment, multilayer hydrogels are described herein. It is appreciated that multilayer hydrogels may advantageously include two or more hydrogel compositions with the same or similar performance characteristics, or alternatively, two or more different hydrogel compositions, each with potentially different performance characteristics. For example, a first layer may be used to deliver a first drug, and a second layer may be used to deliver a second drug. Each layer may be prepared to possess different degradation characteristics to control drug delivery. In another embodiment, a first layer may be used to deliver a population of cells, and a second layer may be used to deliver a drug. Each layer may be prepared to possess different degradation characteristics to control cargo delivery. As described herein, each hydrogel layer may be prepared without the requirement of a co-initiator, or a co-monomer, each of which may be cytotoxic. It is to be understood that, although not required, additional initiator may be advantageously added in forming additional hydrogel layers.

Conventional multilayer hydrogels have been previously described; however, when using such conventional multilayer hydrogels, the fabrication of the second layer requires the production and release of hydrogen peroxide, which may be cytotoxic. For example, a conventional multilayer hydrogels have been previously described based on glucose oxidase mediated polymerization. In that system, the formation of a double-layered hydrogel is initiated by the diffusion of the encapsulated glucose which reacts with glucose oxidase to produce hydrogen peroxide and further generates radicals. The surface-mediated polymerization includes the production of cytotoxic hydrogen peroxide as well as the complicated process and parameters for the formation of the surface hydrogel layer.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenyl and/or alkynyl groups, including $C_2$-$C_8$, $C_2$-$C_6$, and $C_2$-$C_4$ may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkylene groups, including $C_1$-$C_8$, $C_1$-$C_6$, and $C_1$-$C_4$ may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenylene and/or alkynylene groups, including $C_2$-$C_8$, $C_2$-$C_6$, and $C_2$-$C_4$ may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

Each of the publications or other references cited herein are incorporated herein by reference.

The following examples further illustrate specific embodiments of the invention; however, the following illustrative examples should not be interpreted in any way to limit the invention.

EXAMPLES

EXAMPLE. Materials: Eosin-Y disodium salt, triethanolamine (TEOA) and N-vinyl-2 pyrrolidinone (NVP) from MP Biomedical, Alfa Aesar and Acros Organics, respectively. 4-arm PEG-OH (20 kDa) and 4-arm PEG-amine are purchased from JenKem Technology USA. 2-arm PEG-OH (10 kDa) and all other chemicals are obtained from Sigma-Aldrich unless noted otherwise.

EXAMPLE. Synthesis of PEG macromers: Poly(ethylene glycol)-tetra-norbornene (PEG4NB), poly(ethylene glycol)-di-norbornene (PEGdNB) and Poly(ethylene glycol)-diacrylate (PEGDA) are synthesized using conventional processes. Poly(ethylene glycol)-tetra-amide-norbornene (PEG4aNB) is synthesized as described herein. In brief, oxalyl chloride (5-fold excess to norbornene acid) in anhydrous dichloromethane (DCM) and dimethylformamide (DMF) is added dropwise to a round flask containing norbornene acid (5-fold excess to amine groups on PEG-amine) in 2 mL of DCM. After 2 hours of reaction, excess oxalyl chloride is removed using a rotary evaporator. The norbornene-acyl chloride product is added dropwise to another round flask containing dissolved PEG-amine (in tryethylamine and DCM). After overnight reaction, the volume of the product is reduced by using a rotary evaporator followed by precipitation in 4° C. ethyl ether. The product is then filtrated, re-dissolved in minimum amount of DCM, and re-precipitated in 4° C. ether. $^1$H NMR is used to confirm high degree of PEG functionalization (>90%).

EXAMPLE. Synthesis of PEG macromers: Poly(ethylene glycol)-tetra-norbornene (PEG4NB) and poly(ethylene glycol)-di-norbornene (PEG2NB) are synthesized using conventional processes. Briefly, in a round flask, 5-norbornene-2-carboxylic acid (5× of —OH group on multi-arm PEG) and coupling reagent N,N'-dicyclohexylcarbodiimide (DCC, 2.5× of —OH group) in anhydrous dichloromethane (DCM) are stirred at room temperature for 30 minutes. The resulting norbornene anhydride is vacuum filtered into an addition funnel where norbornene anhydride is added to a flask containing 4-arm PEG-OH (20 kDa) or 2-arm PEG-OH (10 kDa), 4-(dimethylamino) pyridine (DMAP, 0.5× of —OH group), and pyridine (5× of —OH group) in DCM (kept in an ice bath). After overnight reaction, the product is washed with 5% sodium bicarbonate solution twice and brine once, followed by precipitation in 4° C. ethyl ether. The product is then filtrated, re-dissolved in minimum amount of DCM, and re-precipitated in 4° C. ether. Poly(ethylene glycol)-diacrylate (PEGDA) is synthesized by reacting 2-arm PEG-OH (10 kDa) with acryloyl chloride (4× of —OH group) in the presence of triethylamine (TEA, 4.4× of —OH group) in toluene. After overnight reaction, the solution is filtered through a thin layer of neutral aluminum oxide. Sodium carbonate is added to the solution and the heterogeneous solution is stirred for 2 hours in the dark. The solution is then filtered through Hyflo filtration and the clear solution obtained is precipitated in cold ether. $^1$H NMR is used to confirm high degree of PEG functionalization (>90%).

EXAMPLE. Microwave-assisted solid-phase peptide synthesis (SPPS): The peptide, CRGDS (SEQ ID NO:3), is synthesized and cleaved in a microwave peptide synthesizer (CEM Discover SPS) following standard solid phase peptide synthesis procedure using Fmoc-protected amino acids. Cleaved peptide is precipitated in cold ether, dried in vacuo, purified by reverse phase HPLC (PerkinElmer Flexar system), and confirmed high purity with TOF mass spectrometry (>90%, Agilent Technologies).

Figure 2:
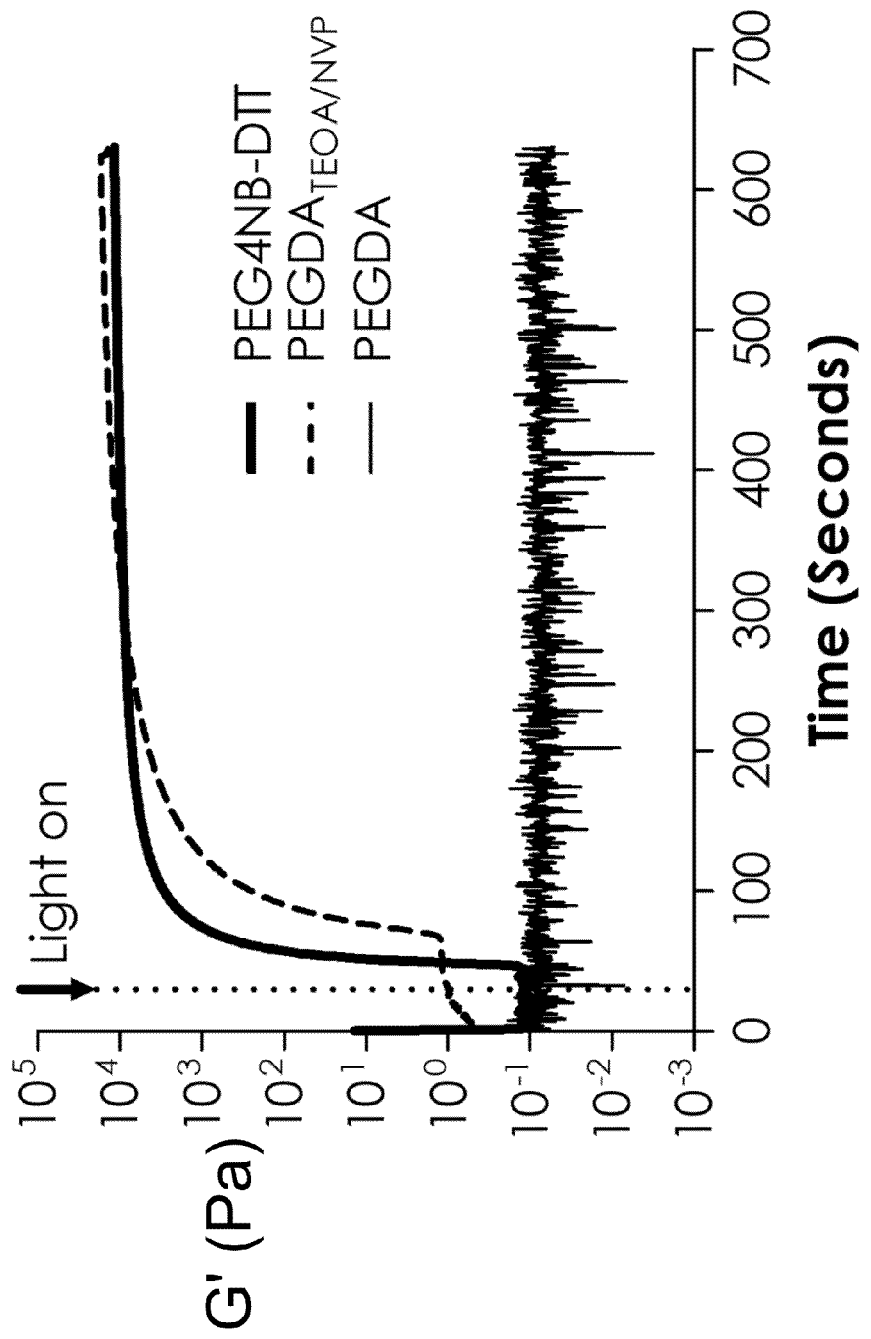
FIG. 2 shows in situ photo-rheometry of PEG hydrogels formed by visible light initiated step-growth thiol-ene photo-click reaction compared to chain-growth polymerizations. Visible light (70,000 Lux) was turned on at 30 seconds. Gel compositions: 10 wt % PEG macromer, and 0.1 mM of eosin-Y in each case; 0.75 vol % TEOA, and/or 0.1 vol % of NVP included in PEGDA$_{TEOA/NVP}$ example. N=3; error bars are omitted for clarity.

COMPARATIVE EXAMPLE. Hydrogel fabrication and swelling: Step-growth thiol-ene hydrogels is formed by radical-mediated photopolymerization between macromer PEG4NB and dithiothreitol (DTT) at a unity molar ratio between thiol and ene groups. Chain-growth PEGDA hydrogels are formed from visible light (argon ion laser) mediated photopolymerization with the addition of co-factor 0.75 vol % of TEOA and co-monomer 0.1 vol % NVP. Both thiol-ene and chain-growth photopolymerizations are initiated by 0.1 mM eosin-Y under visible light exposure (515 nm, 10 mW/cm$^2$) in double distilled water (ddH$_2$O) or aqueous buffered solutions for 4 minutes. Illustrative data for this comparative example is shown in FIG. 2.

Figure 3:
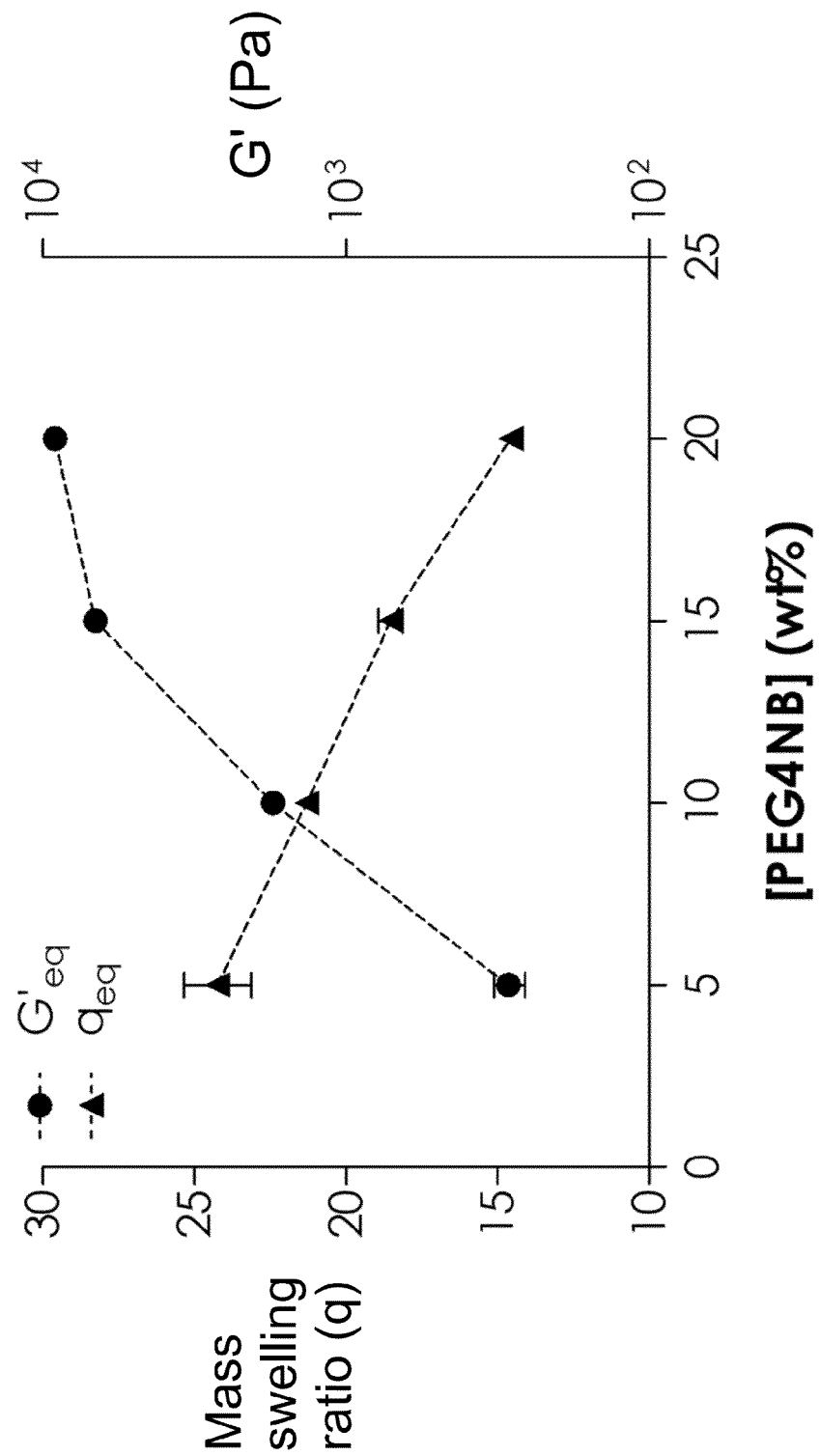
FIG. 3 shows in situ photo-rheometry: Effect of PEG4NB macromer concentration on equilibrium mass swelling ratio ($q_{eq}$ left y-axis) and elastic modulus (G', right y-axis). Mean±SD, N=3.

For swelling studies, circular hydrogel discs (8 mm in diameter and 1 mm in height) are prepared from 50 μL precursor solution. Immediately after gelation, hydrogels are incubated in ddH$_2$O at 37° C. on an orbital shaker for 24 hours to remove sol fraction. Gels are then dried and weighed to obtain dried polymer weights ($W_{Dry}$). The dried polymers are then incubated in 5 mL of buffer solution (pH 7.4 PBS) at 37° C. on an orbital shaker. At equilibrium swelling (after 48 hours), hydrogels are removed from the medium, blotted dry with Kimwipe, and weighed to obtained swollen weights ($W_{Swollen}$). Hydrogel mass swelling ratios (q) are determined by a ratio of $W_{Swollen}$ and $W_{Dry}$. Illustrative data for this comparative example is shown in FIG. 3.

EXAMPLE. Rheometry: For rheometrical property measurements, hydrogel discs (8 mm in diameter and 1 mm in height) are fabricated as described previously and placed in pH 7.4 PBS for 48 hours. Strain sweep (0.1% to 20%) oscillatory rheometry is performed on a Bohlin CVO 100 digital rheometer. Shear moduli of the hydrogels are measured using a parallel plate geometry (8 mm) with a gap size of 800 μm. Tests are performed in the linear viscoelastic region (LVR). In situ gelation rheometry for hydrogels is conducted in a light cure cell using a parallel plate geometry (25 mm) at room temperature. Briefly, the macromer solution is placed on a quartz plate in the light cure cell, and irradiated with visible light (515 nm, 10 mW/cm$^2$) through a visible light guide. Visible light is turned on 30 seconds after the time sweep in situ rheometry. This time sweep in situ rheometry is performed with 10% strain, 1 Hz frequency, 0.1 N normal force, and a gap size of 100 μm. Gel point (i.e., crossover time) is determined at the time when storage or elastic modulus (G') surpassed loss or shear modulus (G").

EXAMPLE. Eosin-Y retention: PEG4NB-DTT hydrogel discs (8 mm in diameter and 1 mm in height) are fabricated. Immediately after polymerization, each hydrogel (8 mm in diameter and 1 mm in height) is immersed into a scintillation vial containing 2 mL of ddH$_2$O. Three separate samples are prepared per experimental condition. These scintillation vials are capped tightly and stored at 37° C. on an orbital shaker. At specific time points, these vials are swirled manually to ensure homogeneous mix and 200 μL of solution is transferred to a well of a transparent 96-well plate. The buffer is changed at every time point. The absorbance (at 515 nm) of the collected samples is determined using a microplate reader (Biotek). Eosin-Y retention was calculated by generating a standard curve prepared from a series of known eosin-Y concentrations (0.02 mM being the highest).

EXAMPLE. Spectrophotometry of eosin-Y: Precursor solutions (200 μL each, 3 samples per condition) contained 0.02 mM of eosin-Y and non-gelling components (PEG2NB and DTT) used in gelation studies are mixed and transferred to a transparent 96-well plate. The 96-well plate is exposed to visible light (515 nm, 10 mW/cm$^2$) for 4 minutes. The spectrophotography (wavelength: between 400 to 600 nm) of eosin-Y in the presence of the gelling conditions is determined by a microplate reader (Biotek).

EXAMPLE. Cell encapsulation and cytocompatibility: Desired density (5×10$^6$ cells/mL) of human mesenchymal stem cells (hMSCs) are suspended in polymer solutions (PEG4NB-DTT, PEG4aNB-DTT or PEGDA for step-growth thiol-ene and chain-growth hydrogels, respectively). Polymer solution contained 1 mM of CRGDS (SEQ ID NO:3) for both step-growth thiol-ene and chain-growth PEGDA hydrogels. The hMSC cell-laden PEG hydrogels (25 μL) are supplemented in hMSC growth media (low-glucose DMEM with L-glutamine and sodium pyruvate, 10% fetal bovine serum (FBS), 1 ng/mL bFGF and antibiotic-antimycotic) at 37° C. and 5% of CO$_2$.

For quantitative long-term cell viability study, cell-laden hydrogels are incubated in 500 μL Almarblue® reagent (10% in cell culture medium; AbD Serotec) at 37° C. and 5% of CO$_2$. After 14 hours of incubation, 200 μL of incubated Almarblue® media is transferred to a transparent 96-well plate. Using a microplate reader, the Almarblue® fluorescence (excitation: 560 nm and emission: 590 nm) due to cell metabolic activity is determined. In addition, confocal imaging of hMSCs cell-laden hydrogels are stained with Biotium live/dead kit (Calcein AM stained live cells green and Ethidium homodimer-1 stained dead cells red) for an hour and washed with DPBS for 10 minutes. Four random fields are selected per hydrogel sample and each group composed of three hydrogel samples.

EXAMPLE. Cell encapsulation and cytocompatibility: Desired density (5×10$^6$ cells/mL) of mouse insulinoma cells (MIN6) are suspended in polymer solutions (PEG4NB-DTT or PEGDA for step-growth thiol-ene and chain-growth hydrogels, respectively). Polymer solution contained 1 mM of CRGDS (SEQ ID NO:3) for both step-growth thiol-ene and chain-growth PEGDA hydrogels. The MIN6 cell-laden PEG hydrogels (25 μL) are supplemented in MIN6 growth media (high-glucose DMEM with L-glutamine and sodium pyruvate, 10% fetal bovine serum (FBS), 2 μL β-mercaptoethanol and antibiotic-antimycotic) at 37° C. and 5% of CO$_2$.

For quantitative long-term cell viability study, cell-laden hydrogels are incubated in 500 μL Almarblue® reagent (10% in cell culture medium; AbD Serotec) at 37° C. and 5% of CO$_2$. After 14 hours of incubation, 200 μL of incubated Almarblue® media is transferred to a transparent 96-well plate. Using a microplate reader, the Almarblue® fluorescence (excitation: 560 nm and emission: 590 nm) due to cell metabolic activity is determined. Four random fields are selected per hydrogel sample and each group composed of three hydrogel samples.

EXAMPLE. Hydrogel confocal imaging: At equilibrium swelling, thiol-ene hydrogels (8 mm in diameter and 1 mm in height) are imaged with a confocal microscope (FV1000 Laser Scanning Biological Microscope). The confocal imaging is performed with a step size of 50 μm for a total image thickness of 1 mm. The Z-stack image is displayed in xz-view and the corresponding fluorescence intensity is analyzed by sectioning image into two halves (parallel to the z-axis) in Olympus FluoView software.

EXAMPLE. Multilayer hydrogel: The pre-formed PEG4NB-DTT hydrogel (25 μL) is fabricated as described herein in an open 1 mL syringe. Immediately after gelation, the gel is placed within a 8 mm hole spacer on a glass slide. PEG4NB-DTT macromer solution containing 5% of Fluoresbrite® Carboxy Microspheres (Polysciences) are transferred to fill the 8 mm hole. The setup is immediately exposed to visible light at 10 mW/cm$^2$. After the second step of polymerization, un-polymerized macromer solution is removed and hydrogel is washed twice and incubated with pH 6.0 PBS to prevent gel degradation. The double-layered gel is imaged immediately with Nikon Eclipse Ti fluorescence microscope and image displayed a stacking of red and blue camera shots.

Figure 4:
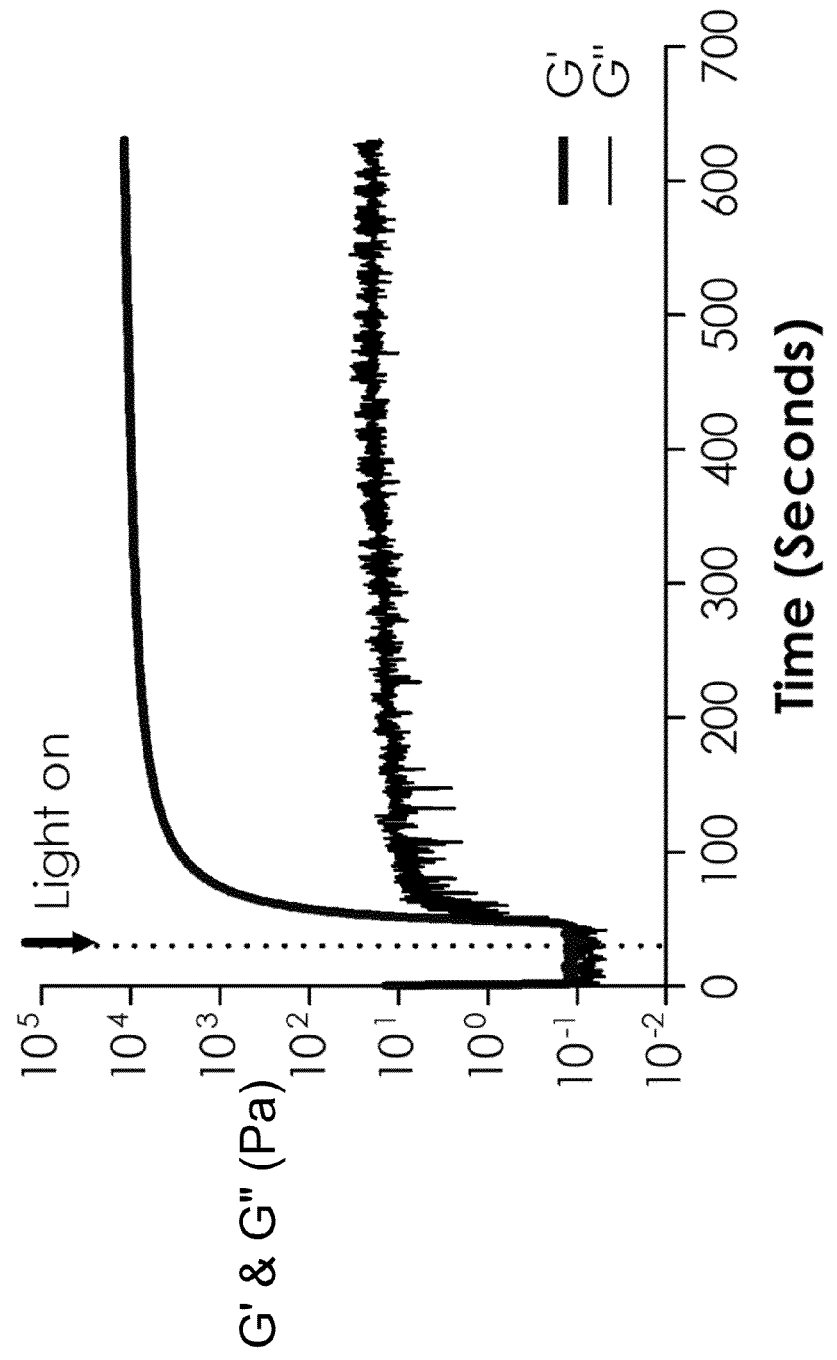
FIG. 4 shows in situ photo-rheometry: Visible light initiated step-growth thiol-ene photo-click polymerization. Gel compositions: 10 wt % PEG macromer, 10 mM dithiothreitol (DTT) crosslinker, and 0.1 mM of eosin-Y (N=3; error bars are omitted for clarity).

As shown in FIG. 4, eosin-Y is excited by a visible light source (halogen cold light, 400-700 nm) to abstract hydrogen atoms from dithiol-containing crosslinkers, such as dithiothreitol (DTT), to form thiyl radicals. The latter propagate through the olefins, such as norbornene moieties, on multi-arm PEG macromers to generate carbonyl radicals, which further abstract hydrogen atoms from other thiol-containing molecules, thus forming a step-growth thiol-ene hydrogel network. The rapid gelation kinetics are achieved without the use of a co-monomer to accelerate gelation. As shown in FIG. 4, FIG. 2 and Table 1, thiol-ene hydrogels prepared by visible light-mediated photo-click reactions exhibit rapid gel points when compared to chain-growth polymerization of PEGDA hydrogels using the conventional eosin-Y/TEOA/NVP initiation system (gel point=19±2 and 37±1 seconds for PEGNB-DTT$_{eosin-Y}$ an PEGDA$_{eosin-Y/TEOA/NVP}$ hydrogels, respectively). Without being bound by theory, it is believed herein that the slightly higher shear modulus in PEGDA hydrogels after 10 minutes of light exposure is potentially due to the use of co-monomer NVP, which has been shown to increase gel modulus.

TABLE 1

Gelation characteristics of thiol-ene hydrogels formed by visible light initiation. (10 wt % PEG macromer, and 0.1 mM of eosin-Y in each case; 0.75 vol % TEOA, and/or 0.1 vol % of NVP included in PEGDA$_{TEOA/NVP}$ example; N = 3)

| Intensity (mW/cm$^2$ @515 nm) | PEG hydrogel | Gel point (seconds) | G'@ 600 sec (kPa) |
|---|---|---|---|
| 3.5* (25,000 Lux)** | PEG4NB | 366 ± 19 | 0.15 ± 0.04 |
| 8.5* (50,000 Lux) | PEG4NB | 114 ± 3 | 1.9 ± 0.5 |
| 10 (70,000 Lux) | PEG4NB | 19 ± 2 | 12 ± 1.5 |
| | PEGDA$_{TEOA/NVP}$ | 37 ± 1 | 17 ± 1.6 |

*At 600 seconds, this light intensity did not yield complete gelation.
**The light source used was a broad spectrum visible light source, including 515 nm.

Figure 5:
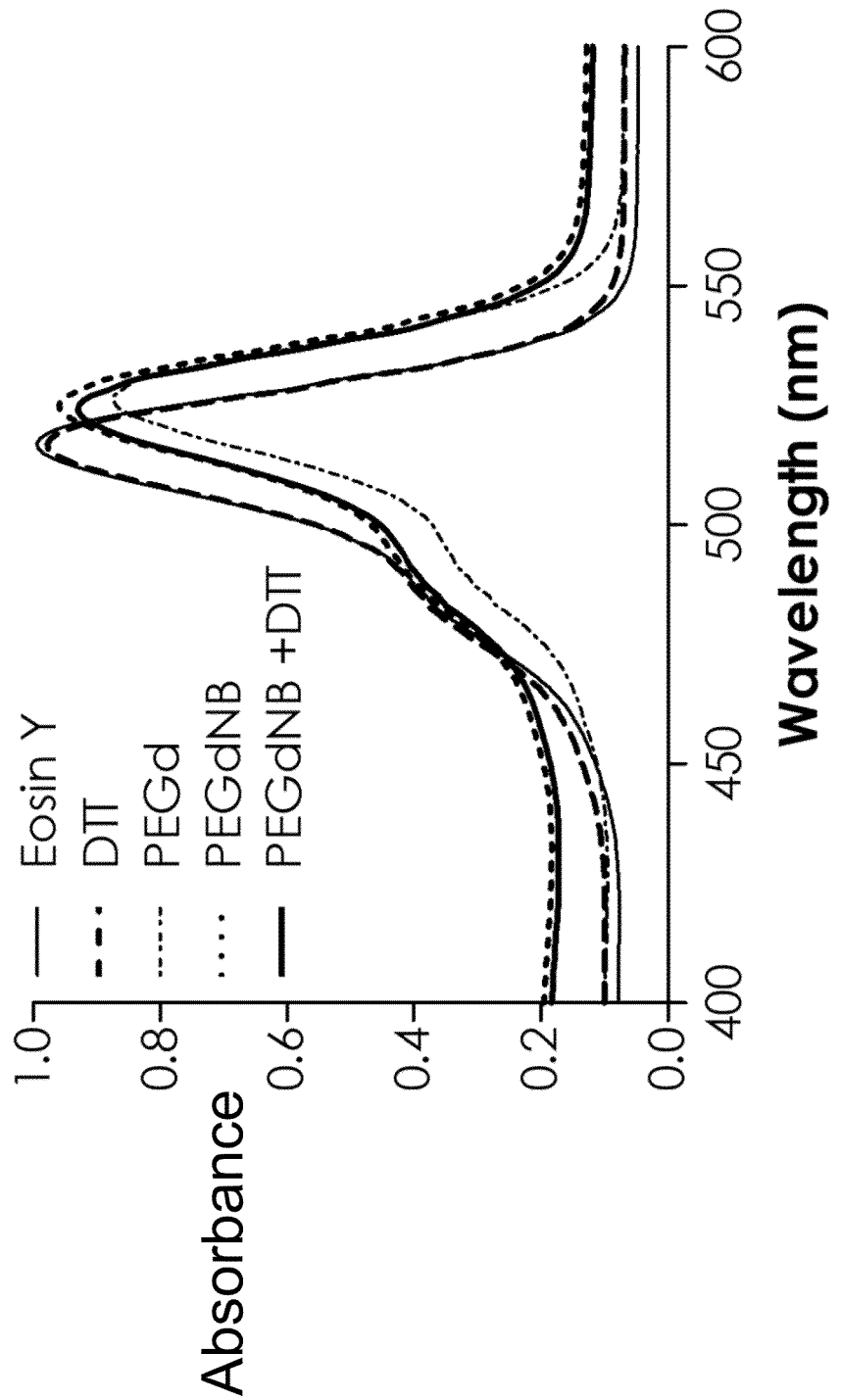
FIG. 5 shows spectrophotometry of eosin-Y after visible light exposure in the presence of different components used in gelation studies. Each curve presents an average of 3 samples and error bars are omitted for clarity. (10 wt % PEG4NB-DTT, 0.02 mM EY, N=3).
Figure 6:
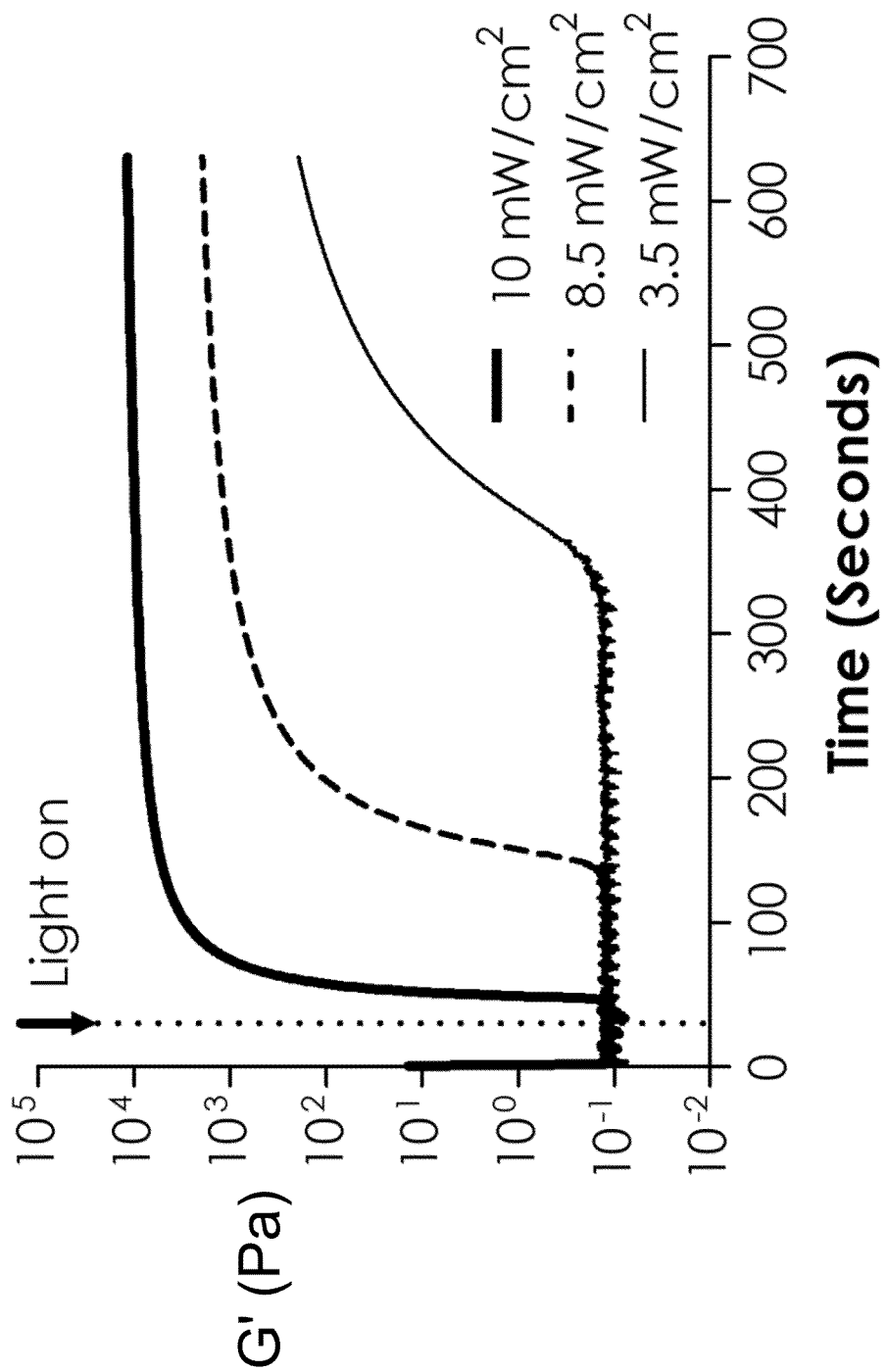
FIG. 6 shows in situ photo-rheometry of thiol-ene hydrogels formed at different light intensity: 70,000, 60,000, and 25,000 Lux. Visible light was turned on at 30 seconds.

EXAMPLE. Examination of gelation kinetics under different light intensities using in situ photo-rheometry. The halogen lamp emits cold lights with wavelengths between 400 to 700 nm, a spectrum largely overlaps with the absorbance spectrum of eosin-Y (450-560 nm, with peak absorbance at 515 nm, FIG. 5). Similar to other photopolymerization systems, gel points and shear moduli of hydrogels formed by visible light-mediated photo-click reactions are observed to decrease with light intensity (FIG. 6 and Table 1). Complete gelation was not obtained after 10 minutes of polymerization at light intensity of 8.5 and 3.5 mW/cm$^2$.

Figure 7:
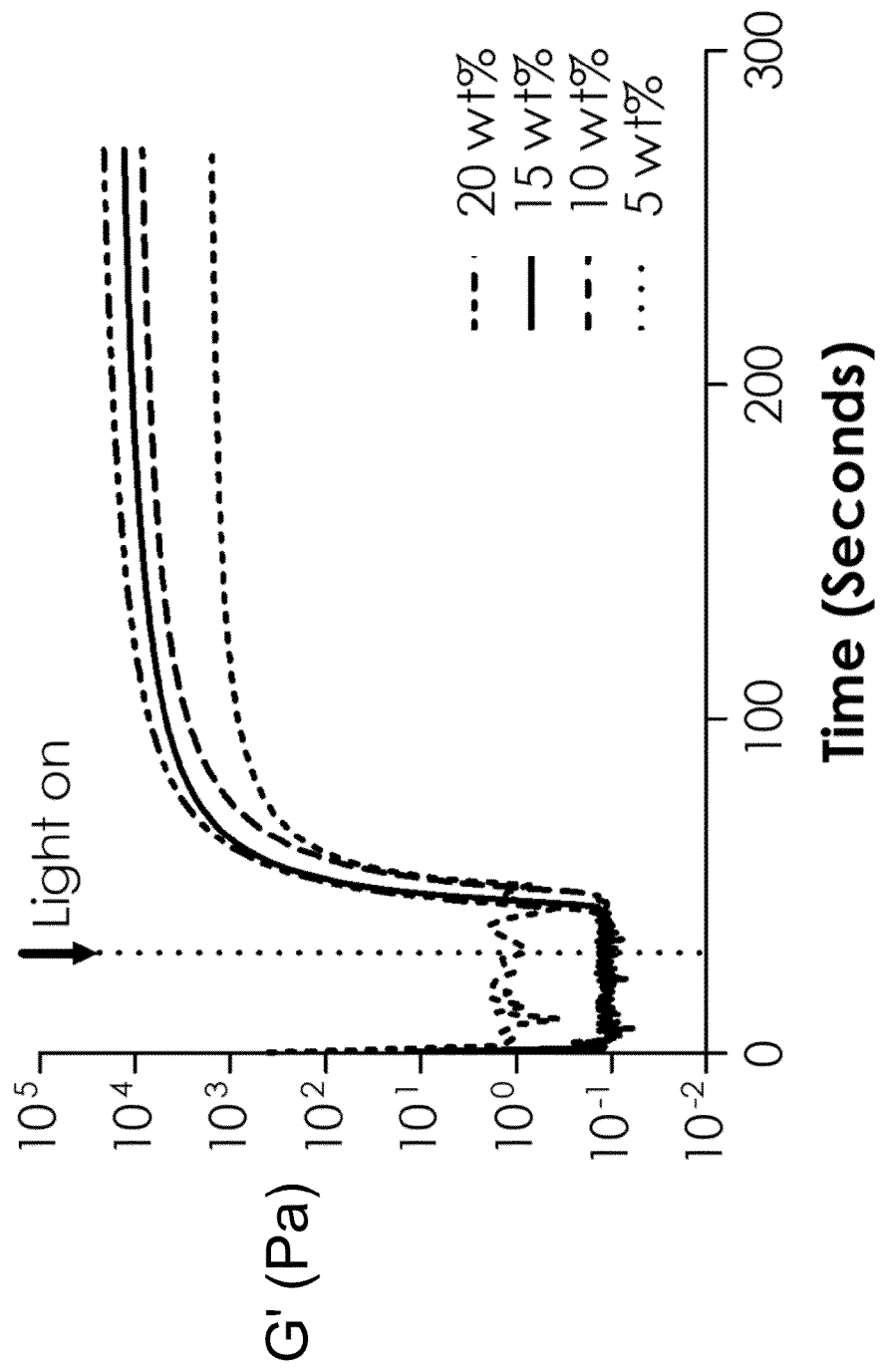
FIG. 7 shows in situ photo-rheometry and the effect of PEG4NB macromer concentration on gelation kinetics.

EXAMPLE. Evaluation of effect of macromer concentrations on visible light-mediated thiol-ene network crosslinking. The polymerization time (4 minutes) was selected based on FIG. 4, where complete gelation was achieved. An inverse correlation between macromer (PEG4NB) concentration and gel point was observed (FIG. 7 and Table 2). Similar to other PEG hydrogel systems, increasing macromer concentration improved network crosslinking (i.e., higher final elastic moduli and high gel fractions at high PEG4NB content). The equilibrium mass swelling ratios of the step-growth hydrogels exhibited high dependency on macromer concentration as shown in FIG. 3. Without being bound by theory, it is believed herein that this result supports the existence of network non-ideality, and may be due to a higher tendency of cyclization at lower macromer wt %. Increasing the thickness of hydrogels increased light attenuation, which resulted in decreased gel fraction and hence increased equilibrium gel swelling (Table 2).

TABLE 2

Gelation characteristics of thiol-ene hydrogels formed by visible light initiation. (10 wt % PEG4NB-DTT, N = 3)

| PEG4NB (wt %) | Eosin Y (mM) | Gel point (seconds) | Gel fraction (%) Gel thickness (mm) | |
|---|---|---|---|---|
| | | | 1 | 3 |
| 5 | 0.1 | 27.0 ± 2.3 | 94.0 ± 2.1 | 80.6 ± 3.1 |
| 10 | 0.1 | 19.8 ± 1.3 | 99.3 ± 1.2 | 90.5 ± 3.3 |
| | 0.5 | 6.7 ± 0.4 | 98.6 ± 1.2 | 88.7 ± 3.2 |
| | 1.0 | 4.2 ± 0.1 | 97.9 ± 2.1 | 84.9 ± 3.7 |
| | 1.5 | 2.4 ± 0.2 | 98.6 ± 1.2 | 82.3 ± 1.6 |
| | 2.0 | 2.0 ± 0.2 | 97.3 ± 1.1 | 72.5 ± 0.7 |
| 15 | 0.1 | 15.6 ± 1.6 | 98.4 ± 0.6 | 93.2 ± 3.6 |
| 20 | 0.1 | 14.4 ± 1.4 | 98.7 ± 0.6 | 95.8 ± 1.3 |

Figure 8:
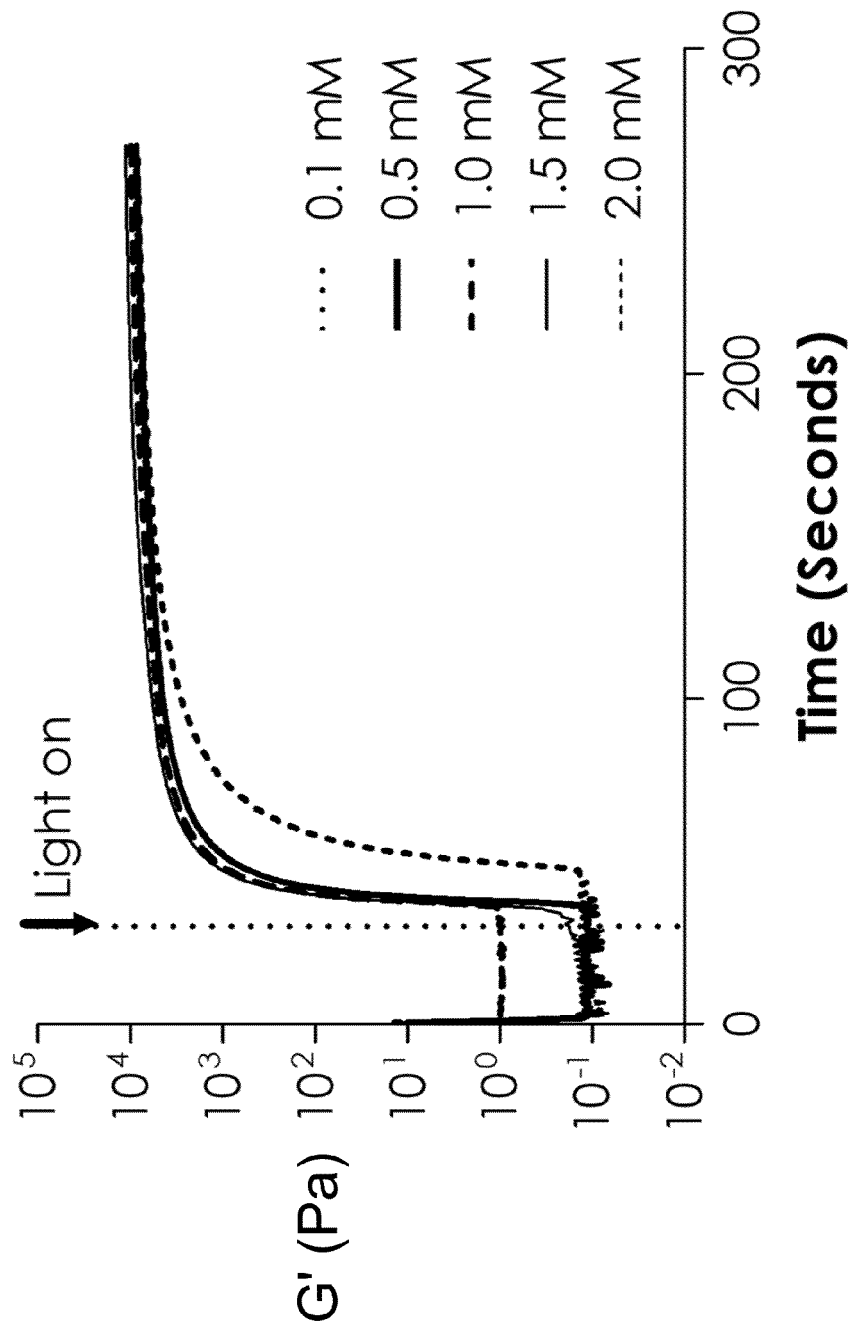
FIG. 8 shows the effect of eosin-Y concentration on gelation kinetics (N=3, error bars are omitted for clarity purpose). Visible light was turned on at 30 seconds.
Figure 9:
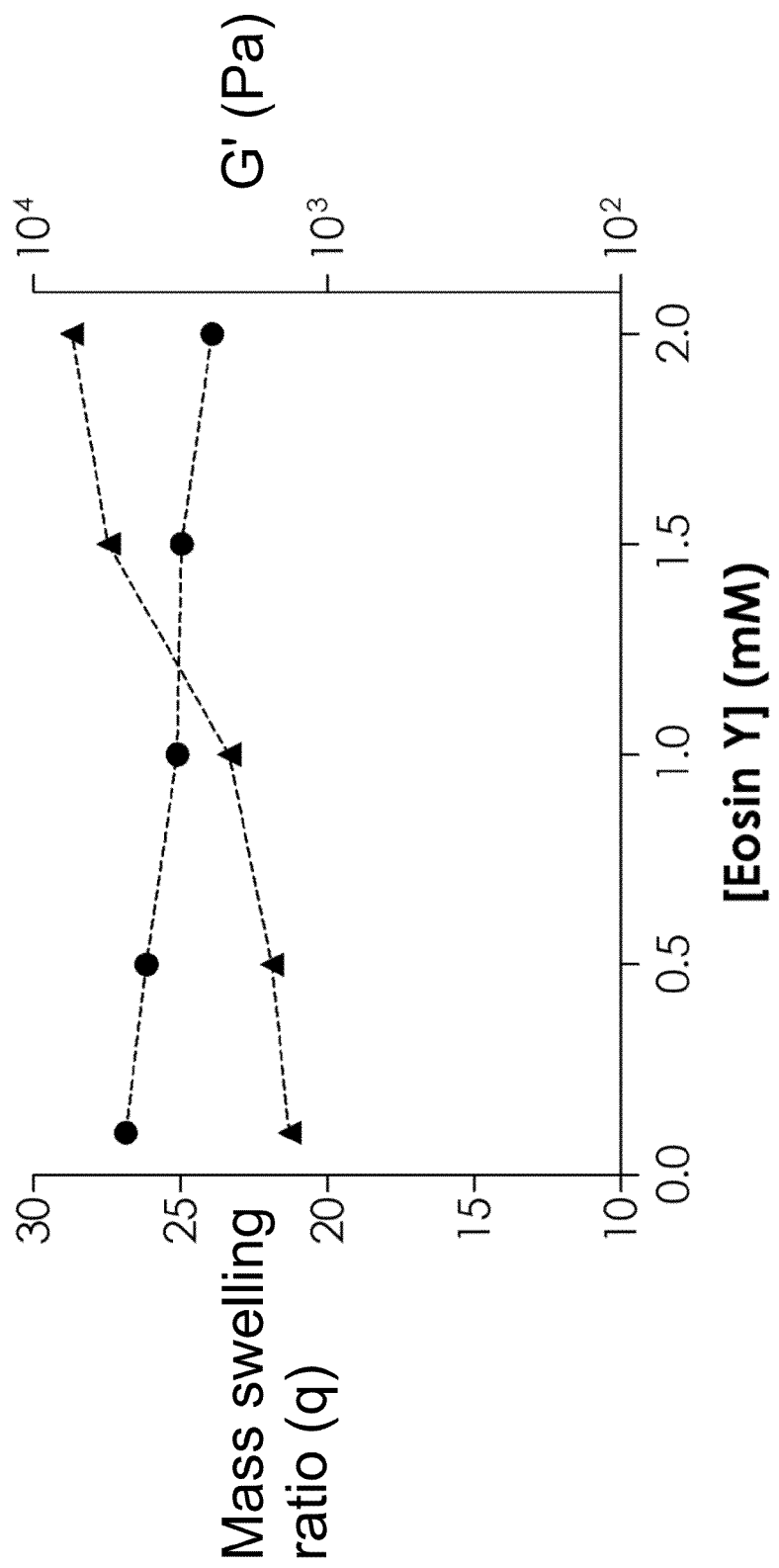
FIG. 9 shows the effect of eosin-Y concentration on equilibrium mass swelling ratio (left y-axis) and elastic modulus (right y-axis).
Figure 10:
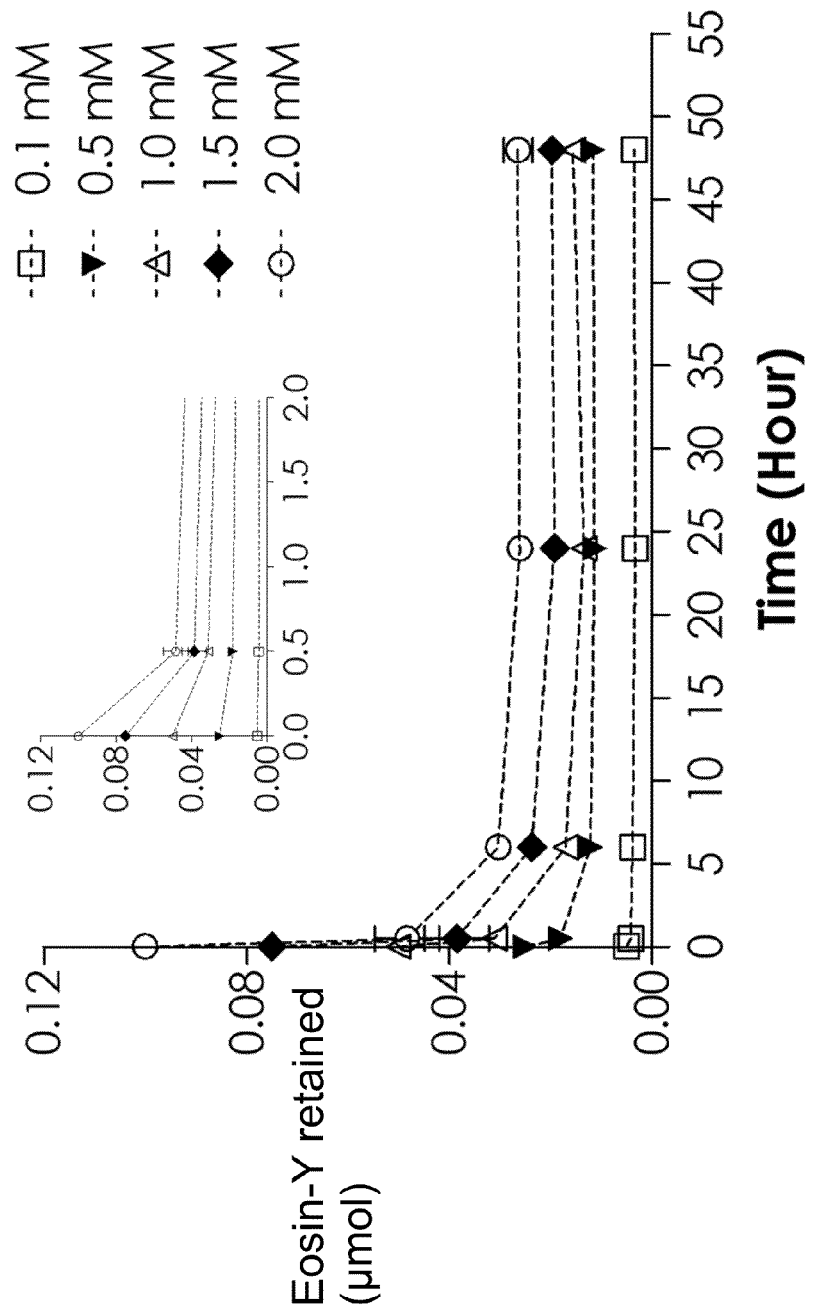
FIG. 10 shows the effect of eosin-Y concentration on eosin-Y retention in thiol-ene hydrogels (eosin-Y concentration increased from 0.1, 0.5, 1.0, 1.5, 2.0 mM after polymerization).

EXAMPLE. Initiation rate as a function of initiator concentration in the polymer precursor solution. Increasing the concentration of eosin-Y decreases gel points (FIG. 8 and Table 2, ~20 versus ~2 seconds for 0.1 to 2 mM of eosin-Y, respectively). The elastic moduli at complete gelation are independent of initiator, such as eosin-Y, concentration. However, it was observed herein that increasing initiator, such as eosin-Y, concentration resulted in decreased gel fraction, which was reflected in higher swelling ratio (q, (▲)) and the lower elastic modulus (G', (●)) at equilibrium swelling (FIG. 9 and Table 2). In the case of eosin-Y, increasing initiator concentration also resulted in deeper red coloring in the hydrogels immediately after polymerization. The red color of those gels may be washed out, and faded significantly after 48 hours of incubation, indicating the release of eosin-Y. FIG. 10 shows that most of the eosin-Y was released in 0.5 hour and a complete release was obtained in 6 hours post-gelation in pH 7.4 PBS.

Higher fluorescence intensity was obtained farther away from the light source, which may be due to photobleaching of eosin-Y during photopolymerization.

However, a significant amount of eosin-Y remained in the gels regardless of the length of swelling time. Without being bound by theory, it is believed herein that eosin-Y exhibits an affinity to these hydrogels. Because eosin-Y has a low molecular weight (691 g/mol), though without being bound by theory, it is not believed that the initiator is trapped within the thiol-ene hydrogels, which have a significantly larger mesh size (~20 nm for 10 wt % PEG4NB-DTT hydrogels). At complete eosin-Y release (after 48 hours of swelling), it was observed that the eosin-Y retention in thol-ene hydrogels was approximately proportional to the starting concentration. Retention increased from ~0.004 to 0.03 μmol as eosin-Y concentration increased from 0.1 to 2.0 mM. FIG. 5 shows the spectrophotometric characteristics of eosin-Y after visible light exposure in the presence of different components used in gelation. While the peak absorbance of eosin-Y was maintained at 515 nm in the presence of DTT, a peak absorbance shift from 515 nm to 525 nm was observed in the presence of PEG species, also suggesting a binding affinity of eosin-Y to PEG.

Figure 11:
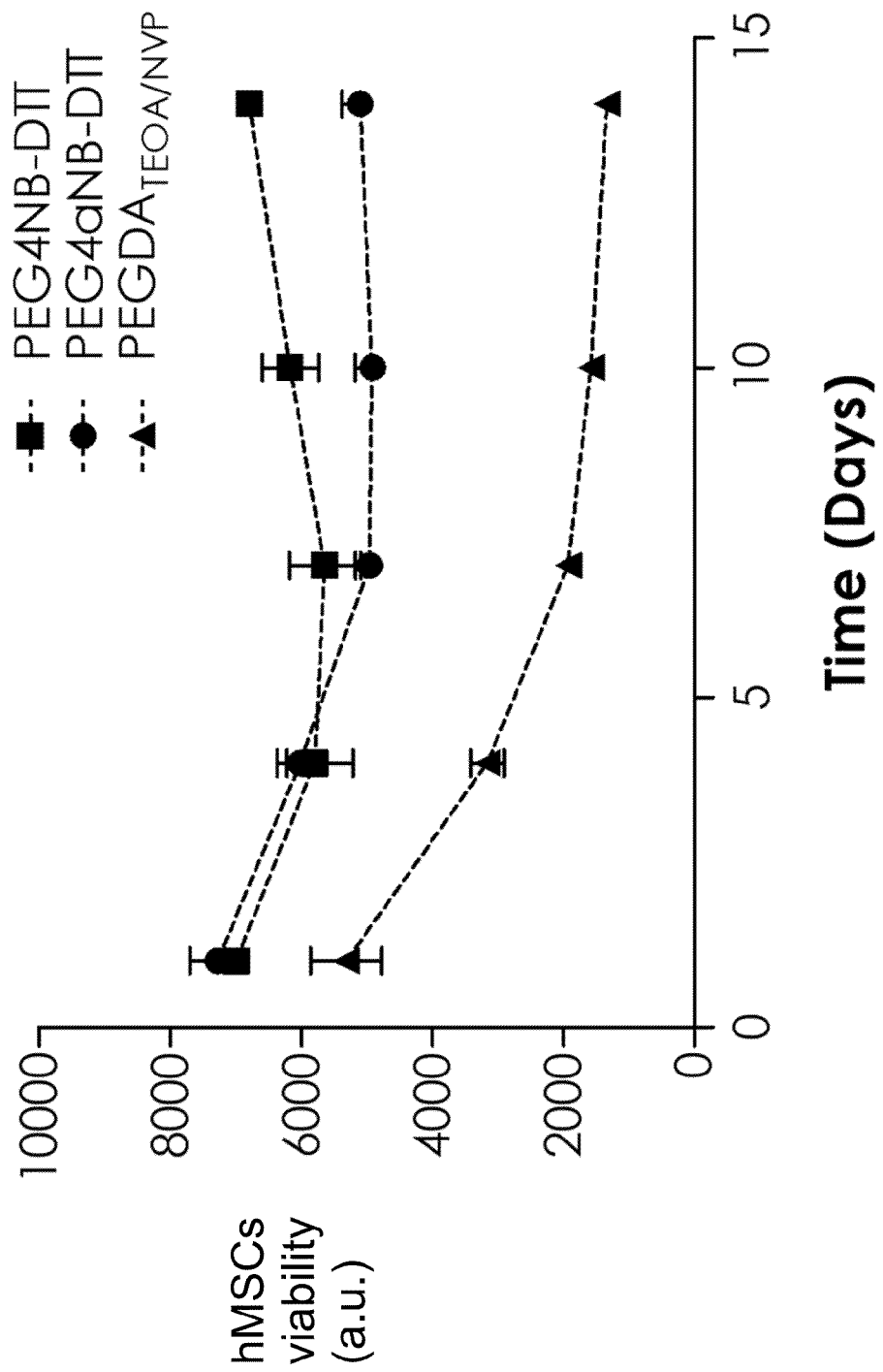
FIG. 11 shows the viability of hMSCs in PEG4NB-DTT, PEG4aNB-DTT or PEGDA hydrogels crosslinked using 0.1 mM eosin-Y. hMSCs viability as time measured with Alamarblue® reagent. (10 wt % PEG hydrogels, cell packing density: 5×10$^6$ cells/mL, 1 mM CRGDS (SEQ ID NO:3), 0.75 vol % TEOA and 0.1 vol % of NVP were used in PEGDA hydrogels, mean±SD, N=3).

EXAMPLE. Cytocompatibility with human mesenchymal stem cells (hMSCs). The cytocompatibility of hydrogels described herein is evaluated using hMSCs (encapsulation density: $5 \times 10^6$ cells/mL). Hydrolytically degradable hydrogels formed by PEG4NB macromer and hydrogels prepared from non-degradable PEG-amide-norbornene macromer described herein are compared to conventional non-degradable chain-growth PEGDA as controls. Both the degradable and non-degradable visible light mediated thiol-ene hydrogels described herein are highly cytocompatible for hMSCs as compared to chain-growth PEGDA system (~95% and ~60% initial viability for thiol-ene and PEGDA hydrogels, respectively). The viability of hMSCs encapsulated in PEGDA hydrogels declined significantly with time, while cells encapsulated in visible light-mediated thiol-ene hydrogels described herein only dropped slightly (FIG. 11). It has been reported that hMSCs viability could be maintained in PEGDA hydrogels formed by visible light-mediated polymerizations in the presence of TEOA and NVP. However, an extremely high cell density ($25 \times 10^6$ cells/mL) was used, which might promote hMSCs survival due to paracrine signaling. Without being bound by theory, it is not believed herein that the higher cell viability in thiol-ene hydrogels is a result of hydrolytic gel degradation (comparative chain-growth PEGDA hydrogels were non-degradable) because controlled experiments using a non-degradable thiol-ene hydrogels crosslinked with PEG4aNB macromer also supported improved hMSCs survival (FIG. 11) compared to the chain-growth PEGDA hydrogel with similar network crosslinking density.

EXAMPLE. Cytocompatibility as a function of initiator concentration. The cytocompatibility of hydrogels crosslinked by different concentrations (0.1 and 1 mM) of eosin-Y is evaluated. Cellular damage was not observed even with the use of high eosin-Y concentration.

Figure 12:
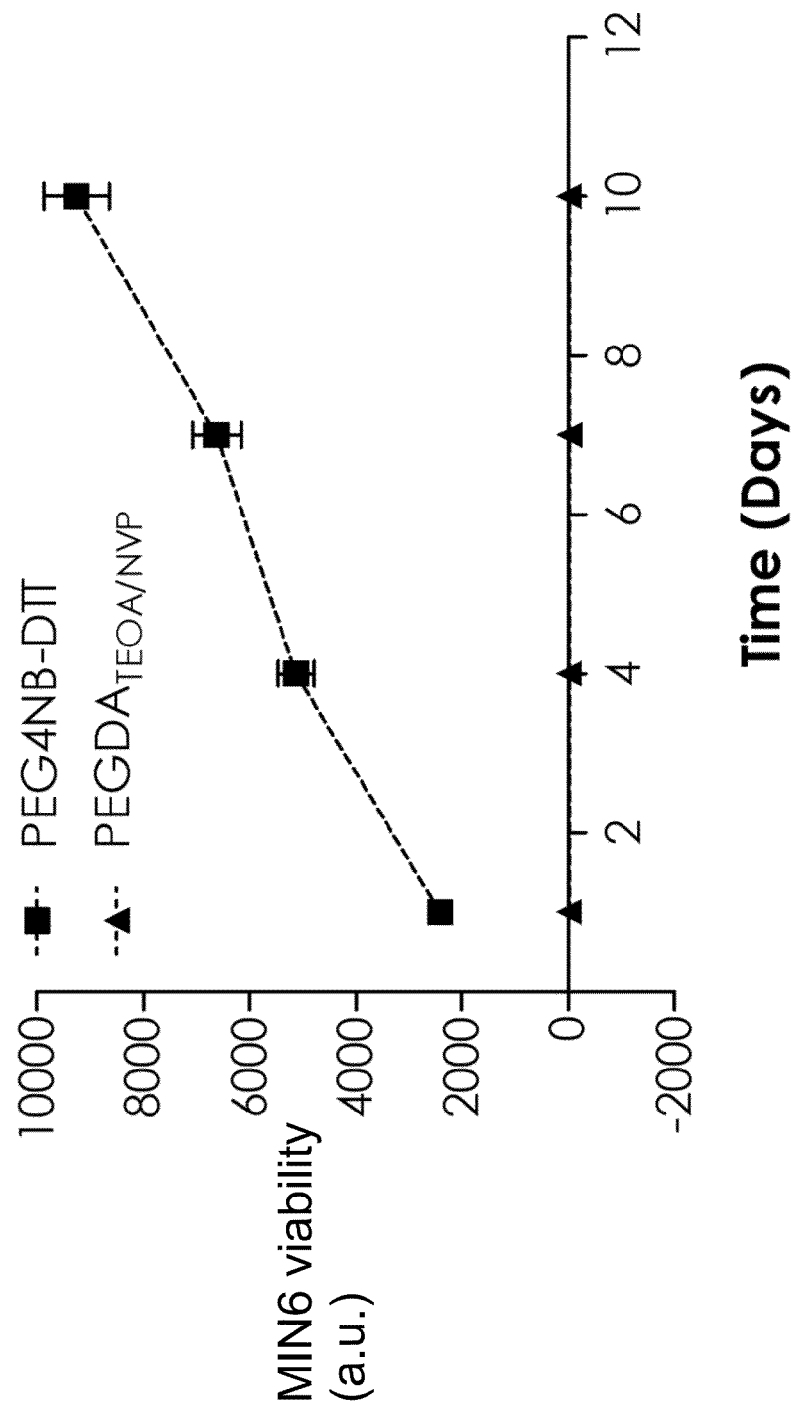
FIG. 12 shows the viability of mouse insulinoma (MIN6) cells in PEG4NB-DTT or PEGDA$_{TEOA/NVP}$ hydrogels crosslinked using 0.1 mM eosin-Y. MIN6 viability quantified by Alamarblue® reagent. (10 wt % PEG hydrogels, cell packing density: 5×10$^6$ cells/mL, 0.75 vol % TEOA and 0.1 vol % of NVP were used in PEGDA hydrogels, N=3, mean±SD).

EXAMPLE. Cytocompatibility with MIN6 cells. The visible light mediated thiol-ene hydrogels are also highly cytocompatible even for the radical sensitive MIN6 β-cells (FIG. 12).

MIN6 cells formed spherical cell aggregates and proliferated (FIG. 12) only in thiol-ene hydrogels (■) but not in PEGDA hydrogels (▲). Without being bound by theory, it is believed herein that the significant cell death in the chain-growth PEGDA system is a collective result of the high concentrations of radical species, formation of dense hydrophobic polyacrylate kinetic chains and cytotoxicity from the necessarily included TEOA and NVP.

Figure 13:
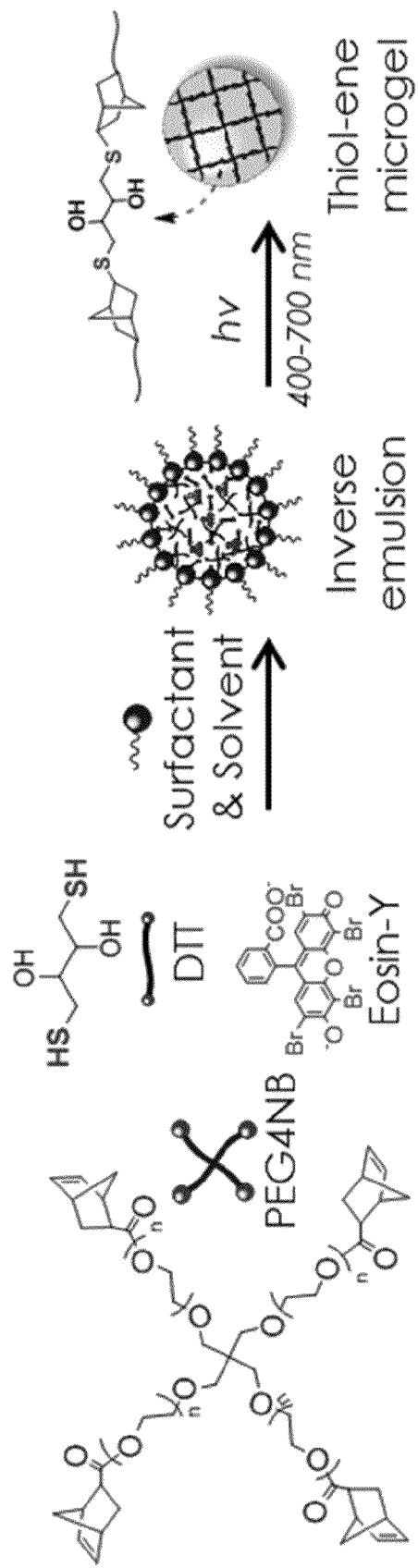
FIG. 13 shows the mechanism for formation of polydisperse thiol-ene microgels.
Figure 14:
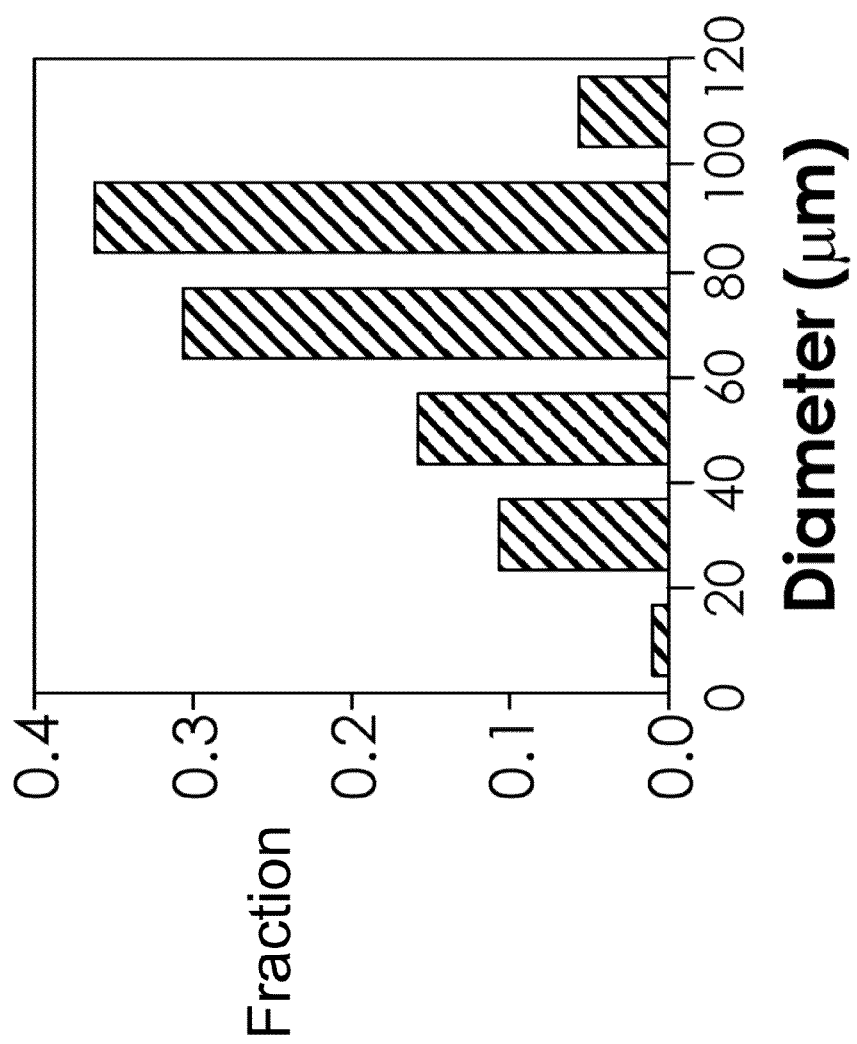
FIG. 14 shows the diameter of formed polydisperse thiol-ene microgels (10-130 μm), with a mean diameter of 70±3 μm.

EXAMPLE. Step-growth thiol-norbornene microgels are fabricated using a visible light source, a re-excitable photoinitiator, hexane as the organic phase, and 1% Span-80/Tween-80 (1:3) as the surfactants. The aqueous pre-polymer solution contained 10 wt. % macromer PEG4NB (10 kDa), cross-linker DTT (at a stoichiometry ratio to norbornene group), and photoinitiator eosin-Y (0.1 mM). Water-in-oil inverse suspension is prepared via vortexing the biphasic system while gel crosslinking was achieved within 30 s of visible light exposure. Polydisperse thiol-ene microgels are formed (10-130 μm) with a mean diameter of 70±3 μm (FIG. 13, FIG. 14).

Figure 15:
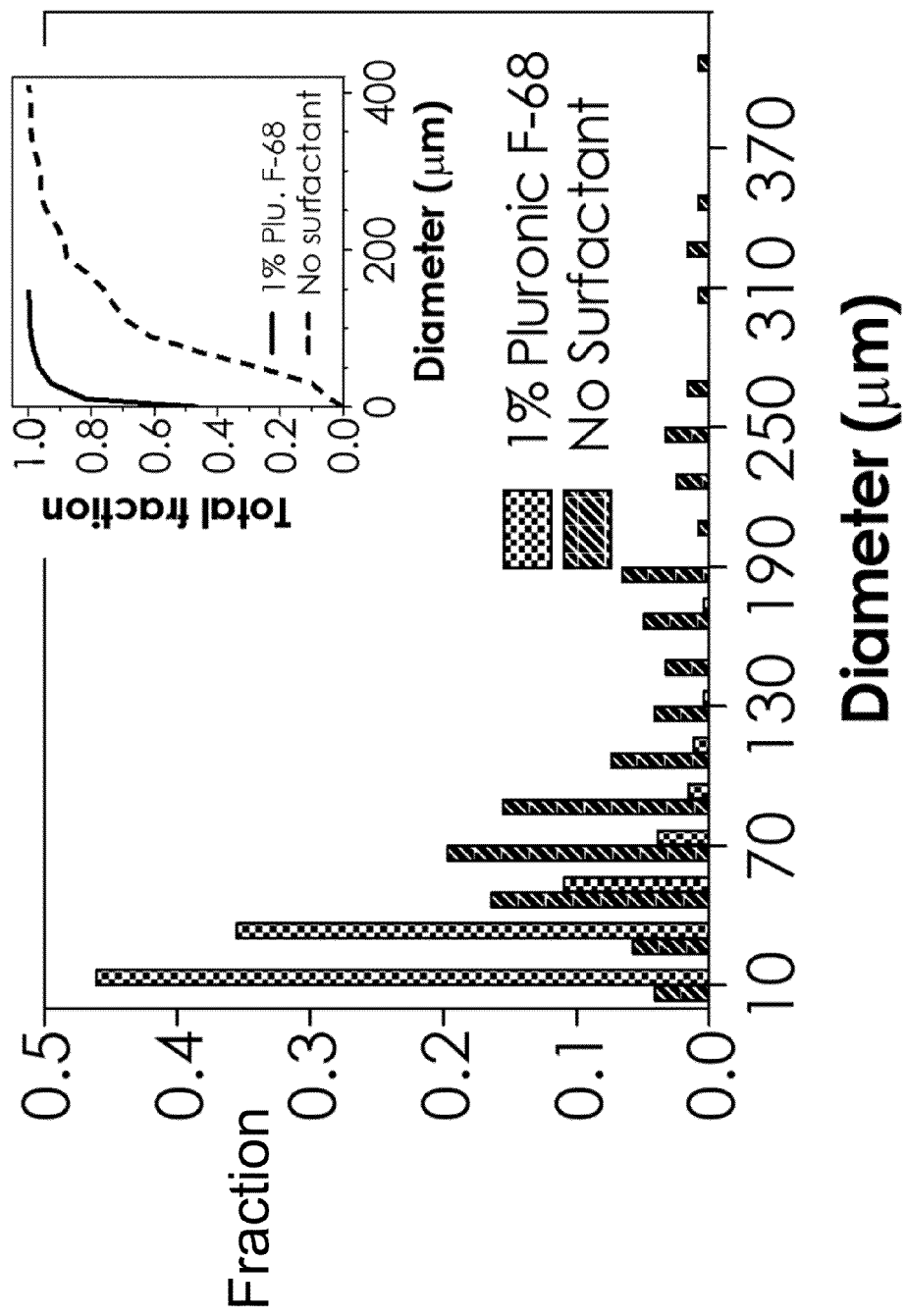
FIG. 15 shows that microgels can be polymerized from the unstable inverse-suspension following 20 s of vortexing, without the use of a surfactant. The microgels have a wide range of sizes and an average diameter of 122 (±21 μm). More than 12% of the microgels formed without emulsifier had diameters higher than 190 μm.
Figure 16:
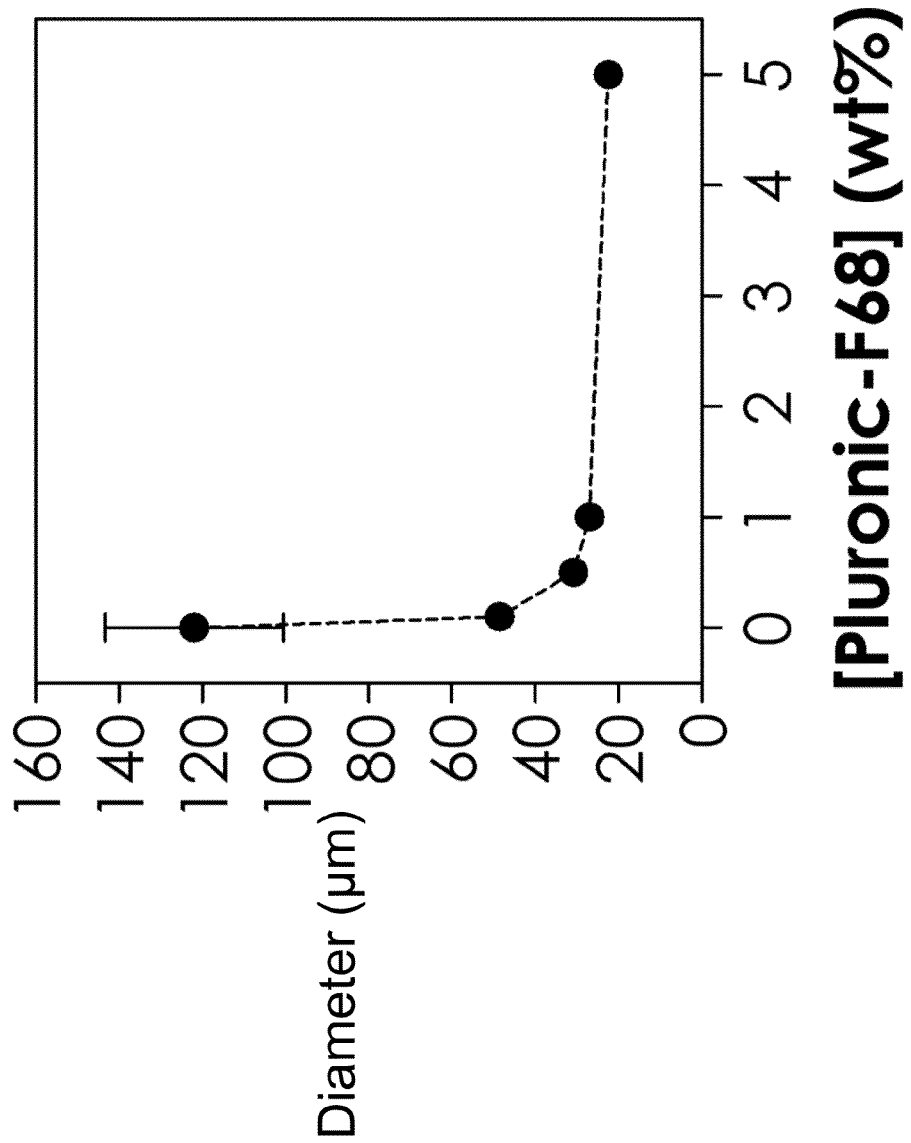
FIG. 16 shows that upon the addition of 1% Pluronic® F-68 as the emulsifier, the inverse-emulsion was stabilized and afforded smaller microgels (average diameter 27±1 μm) and a narrower distribution.

EXAMPLE. Step-growth thiol-norbornene microgels are fabricated using inverse suspension polymerization method with mineral oil as the organic phase and non-ionic cell culture grade Pluronic® F-68 with different concentrations as the surfactant. Without the use of any surfactant, microgels can still be polymerized from the unstable inverse-suspension following 20 s of vortexing (FIG. 15). These microgels have a wide range of sizes and a relatively larger average diameter (122±21 μm). More than 12% of these microgels formed without emulsifier had diameters higher than 190 μm (FIG. 15). When 1% Pluronic® F-68 was added as the emulsifier, the inverse-emulsion was stabilized and afforded smaller microgels with an average diameter of 27±1 μm and a narrower distribution (FIG. 16). 1% of Pluronic® F-68 was sufficient to yield small microgels for this system and further increasing surfactant concentration to 5% does not yield substantially smaller microgels.

Figure 17:
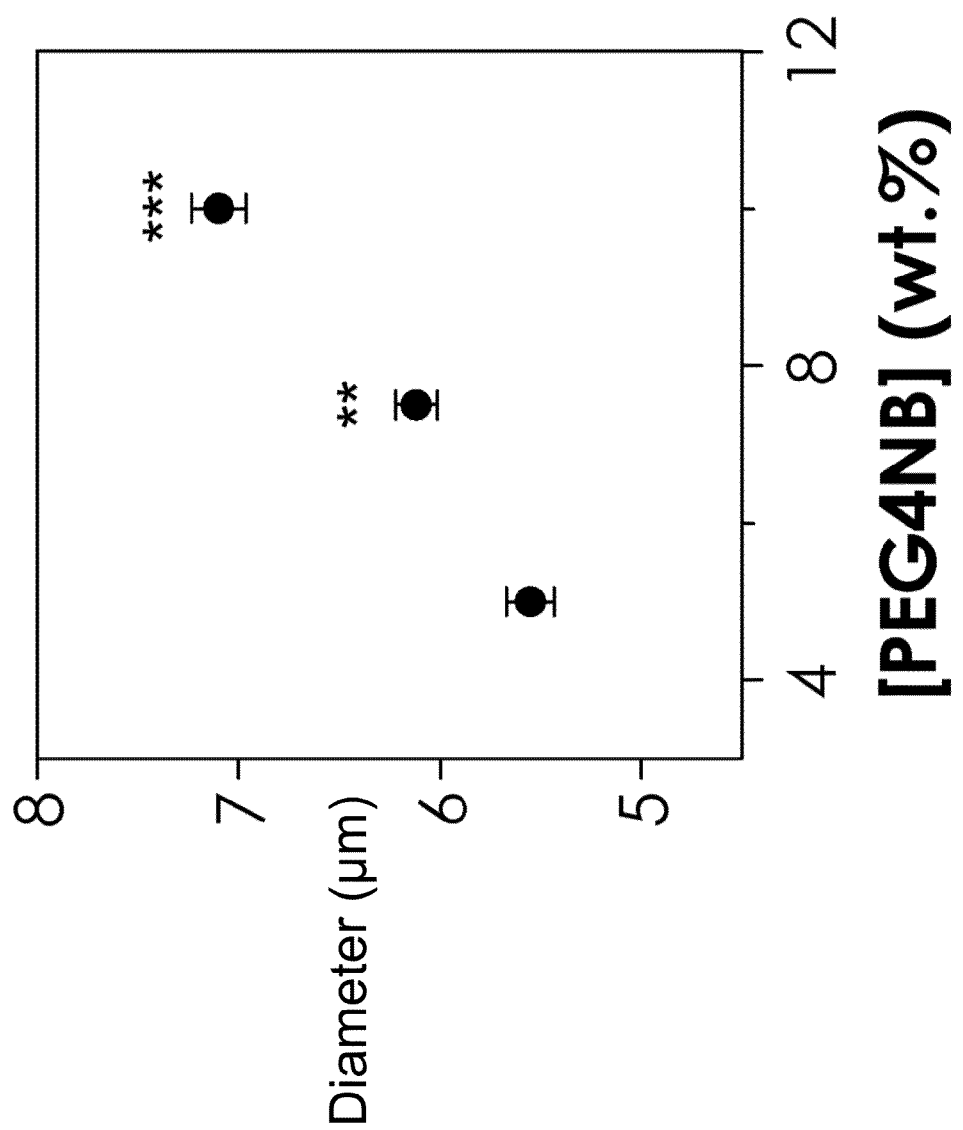
FIG. 17 shows that increasing PEG4NB content (from 5% to 7.5% to 10%) in the pre-polymer solution resulted in an increased average diameter of the microgels.

EXAMPLE. Step-growth thiol-norbornene microgels are fabricated using aqueous two-phase separation. In this process, two immiscible aqueous solutions are mixed together to form discontinuous pre-polymer droplets (e.g., PEG-based macromers) in a continuous aqueous solution (e.g., dextran solution). 40% dextran solution is used as the continuous aqueous phase. After vortexing for 60 s, PEG-based monomer droplets formed in dextran continuous phase and the system is placed under visible light exposure for 4 min. Microgels formed from this aqueous two-phase system are smaller and more uniform in size. Increasing PEG4NB content in the pre-polymer solution increased the average diameter of the microgels, as shown in FIG. 17, where PEG4NB content is increased from 5% to 7.5% to 10%.

Figure 18:
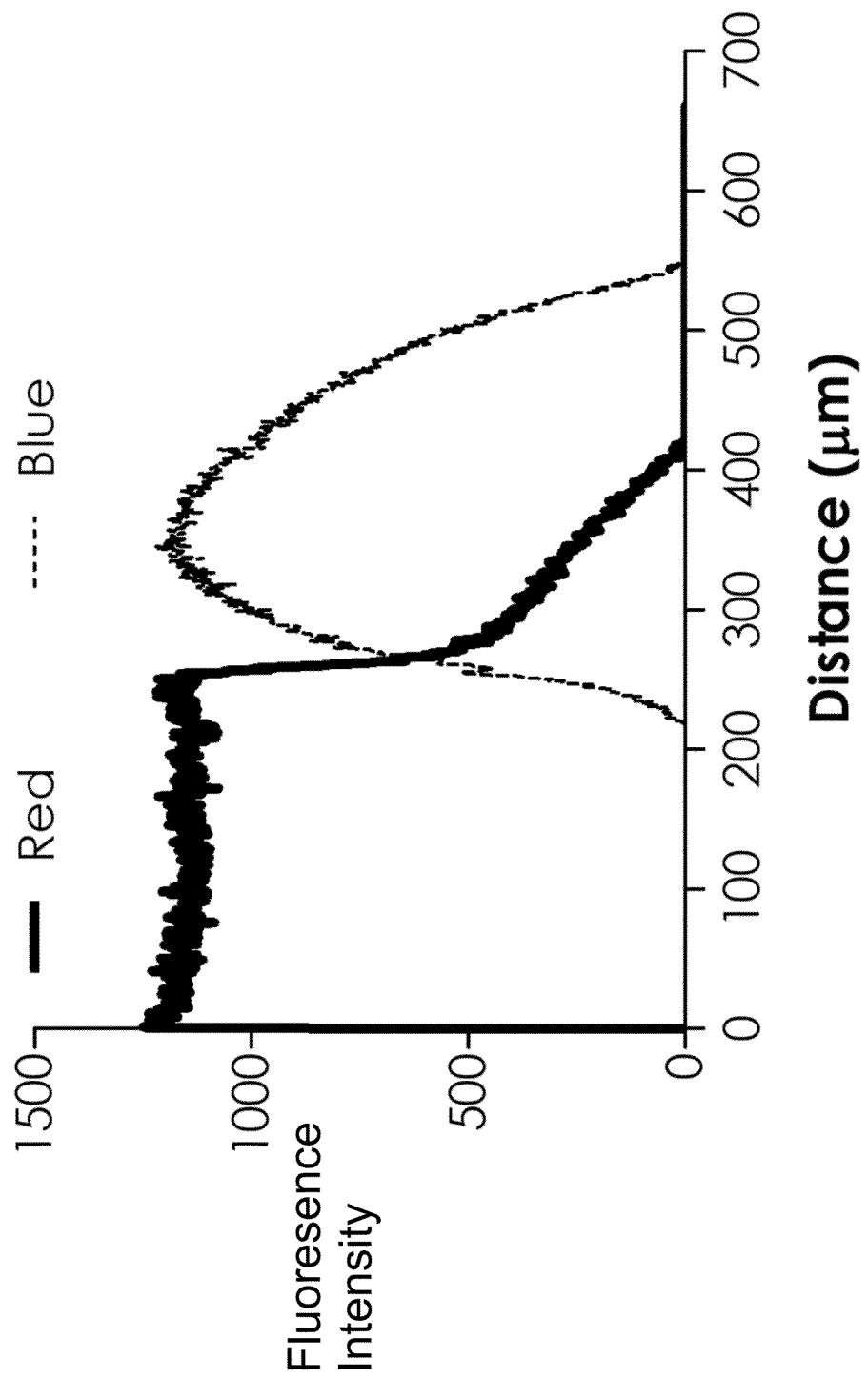
FIG. 18 shows the fluorescence intensity of a double-layered thiol-ene hydrogel (10 wt % PEG4NB-DTT hydrogels, 0.5 mM eosin-Y, 2 minutes of second polymerization, 5% blue particles).

EXAMPLE. Multilayer hydrogels. Thiol-ene hydrogels are fabricated using a high concentration of eosin-Y (e.g., 2 mM). Immediately after gelation, the hydrogel is immersed in a second macromer solution containing only PEG4NB and DTT (blue microparticles are added for imaging purpose). It is appreciated that an additional portion of initiator is optionally added. Upon a second visible light exposure, a thin thiol-ene hydrogel coating is formed. The material is analyzed by fluorescence. Red fluorescence comes from residue eosin-Y while blue fluorescence comes only from the fluorescent microparticles incorporated in the second layer. From the fluorescence intensities of the hydrogel layers, three distinct color areas can be identified: red (from 0 to ~210 μm), purple (from ~210 to 420 μm) and blue (from ~420 to 550 μm) (FIG. 18).

Figure 19:
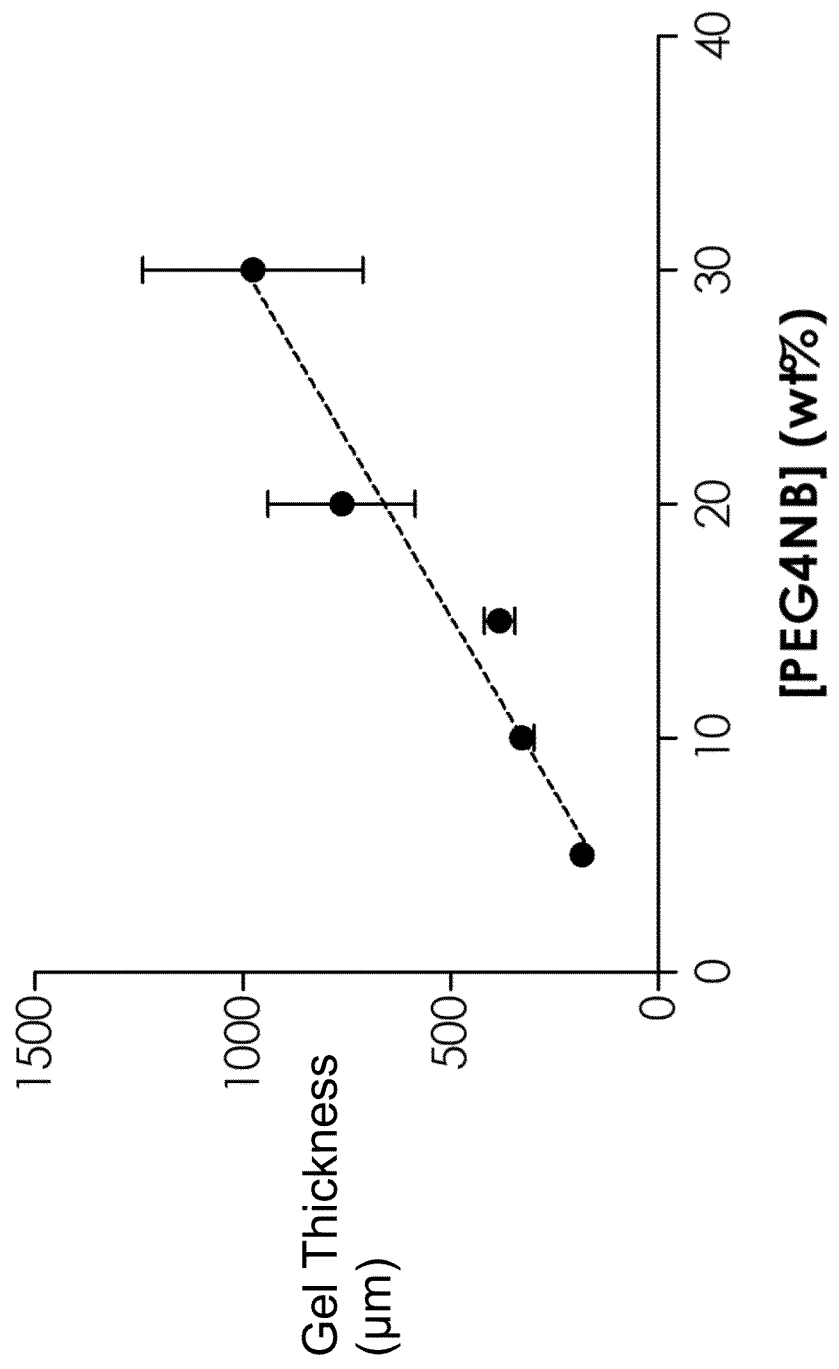
FIG. 19 shows the effect of macromer concentration (2 mM of eosin-Y, 4 minutes of polymerization) used for the pre-formed gel and the time length for the second polymerization. (10 wt % PEG4NB-DTT, 5% blue particles in the second layer, N=3).

Without being bound by theory, the result suggests that the network crosslinking of the second layer is not limited to the presence of eosin-Y (purple band indicates the release of eosin-Y from the core gel) as gel is formed beyond the purple band, as evidenced by the blue band. Though without being bound by theory, it is believed herein that the formation of the double-layered thiol-ene hydrogel is due to the role of both eosin-Y diffusion and surface-mediated polymerization. If the formation of the second gel layer was solely facilitated by the diffusion of the eosin-Y, the thickness of the second layer would be inversely related to the second macromer concentration. An inverse relationship between eosin-Y diffusivity and macromer concentration is assumed. If the gelation of the second layer is mediated by eosin-Y diffusion, thinner gel layers at higher macromer concentration should result. The results herein show the opposite. When the macromer concentration is increased from 5 to 30 wt %, the thickness of the second gel layer increases proportionally from ~180 to ~1000 µm (FIG. 19).

Figure 20:
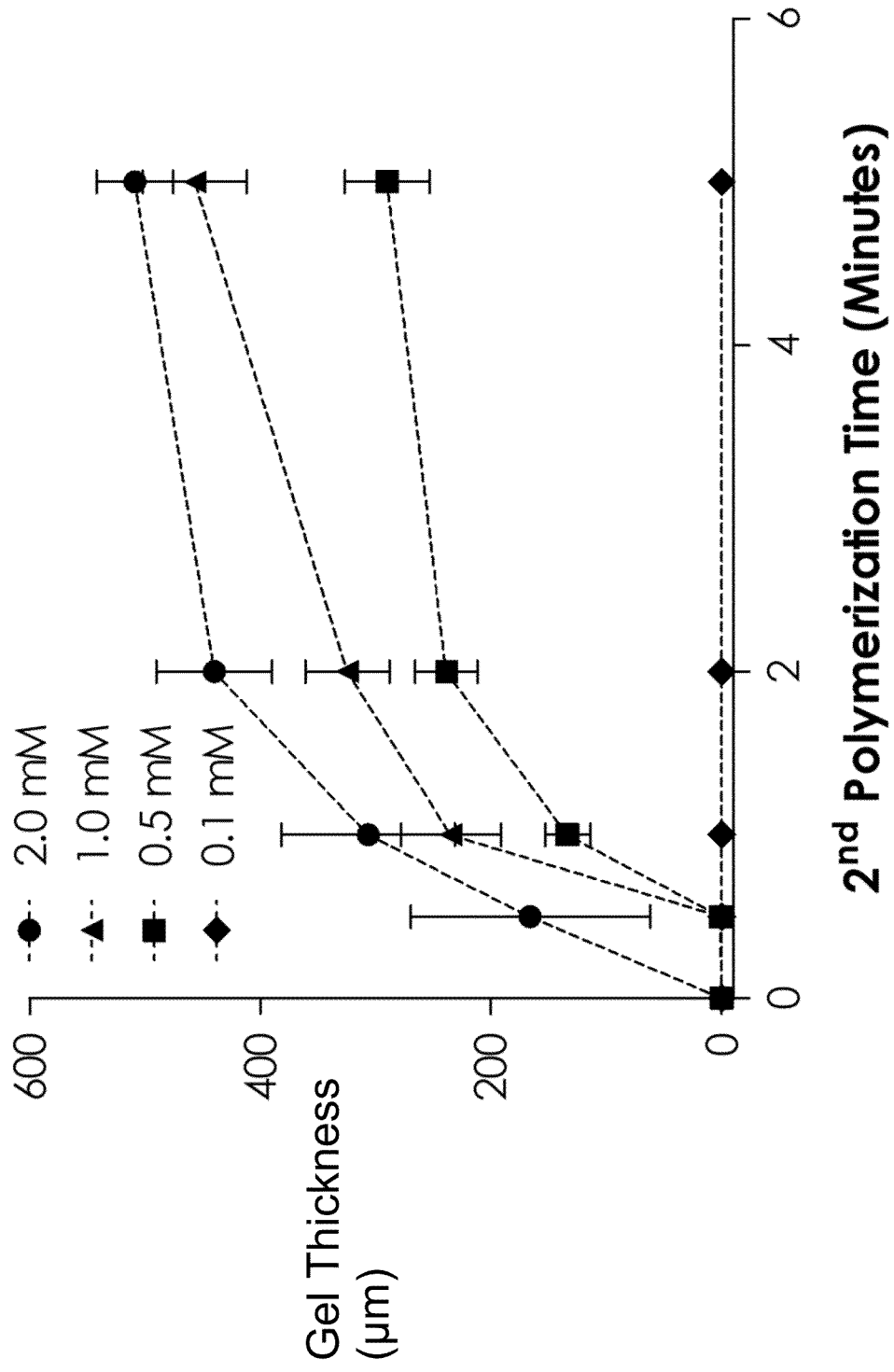
FIG. 20 shows the effect of eosin-Y concentration used for the pre-formed gel and the time length for the second polymerization. (10 wt % PEG4NB-DTT, 5% blue particles in the second layer, N=3).

Based on the eosin-Y retention/release characteristics described herein, the amount of eosin-Y released is approximately proportional to its original concentration in the polymer precursor solution (FIG. 10). It has therefore been discovered herein that the thickness of the second gel layer can be controlled, by increasing either the concentration of eosin-Y or the duration of the secondary visible light exposure. However, the effect of crosslinking time on the second layer gel thickness was not linear or proportional. Instead, the changes in thickness decreased as the polymerization time increased. Without being bound by theory, it is believed herein that these results indicate that surface-mediated polymerization may be dominating (FIG. 20).

Figure 21:
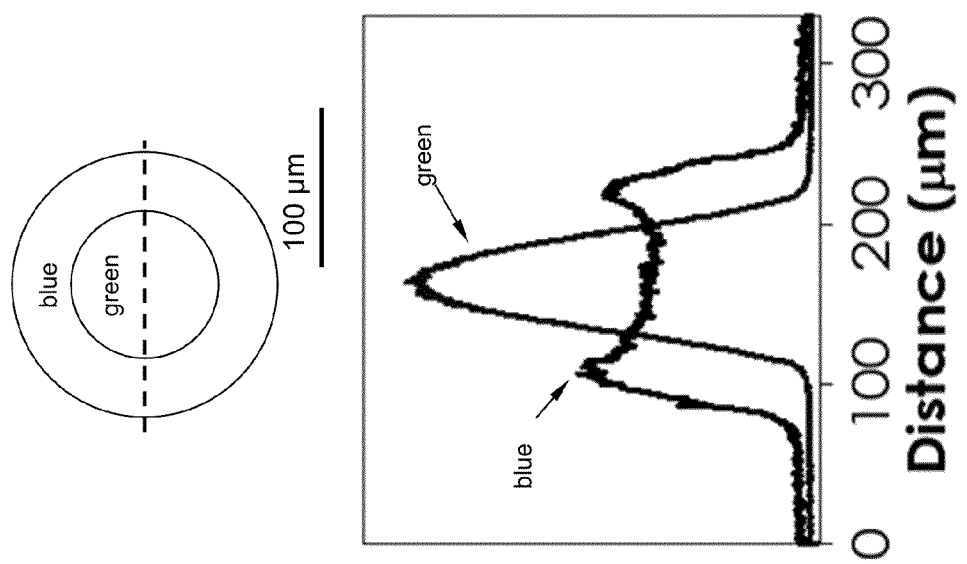
FIG. 21 shows a schematic of a coated core microgel, and the blue and green fluorescence signals for the outer layer and core microgel, respectively. The distance (x-axis) represents the radial scan through the center of the coated microgel.

EXAMPLE. Dual-layer thiol-ene microgels. Dual-layer thiol-ene microgels are prepared by forming the core microgels first, followed by the formation of an interfacial gel layer using the same visible light mediated thiol-ene cross-linking. The pre-polymer solution for preparation of core microgels consisted 10 wt. % PEG4NB-20 kDa, DTT, and 1 vol. % Pluronic-F68. A higher concentration of eosin-Y (2 mM) is used. Core microgels are first formed using the mineral oil method described above and were placed in another pre-polymer solution containing 15 wt. % PEG4NB and DTT. For imaging purpose, 10 vol. % of Fluoresbrite blue microparticles (0.1 µm, Polysciences) are also added in the second pre-polymer solution. The mixture of microgels and the second pre-polymer solution is vortexed for 2 s and exposed to visible light for 5 min. Dual layer thiol-ene microgels are synthesized using visible light mediated thiol-ene polymerization. Green fluorescence in FIG. 21 indicates the presence of residual eosin-y trapped in the core microgel, while blue fluorescence is due to the blue microparticles entrapped in the newly polymerized outer layer. Without light exposure, no noticeable coating is present around the peripheral of the core microgel. After 2 min of visible light exposure, however, a noticeable blue fluorescence layer (20-30 µm thick) is observed around the core microgel, indicating the formation of an interracially cross-linked hydrogel (FIG. 21). It should be noted that no additional initiator component was used to prepare the second gel coating and that the gelation process was initiated interracially from the surface of the core gel. Compared to the prior Example, the outer blue layer is thinner. It is to be understood that the compositions and processes described herein can be adjusted to provide smaller multilayered microgels for use in injectable formats, and the like.

EXAMPLE. Cell surface coating. A population of cells forms a spheroid and is stained with initiator, such as 10 mM EY for 5 minutes, then washed. The stained cells are incubated with a thiol-containing molecule, such as 20 wt % PEG-SH for 5 minutes, then washed. The thiol labeled spheroids are contacted with a macromer and cross-linking agent, such as 10-20 wt % PEGaNB and DTT, and exposed to visible light to form thiol-ene gel coated spheroids.

Figure 22A:
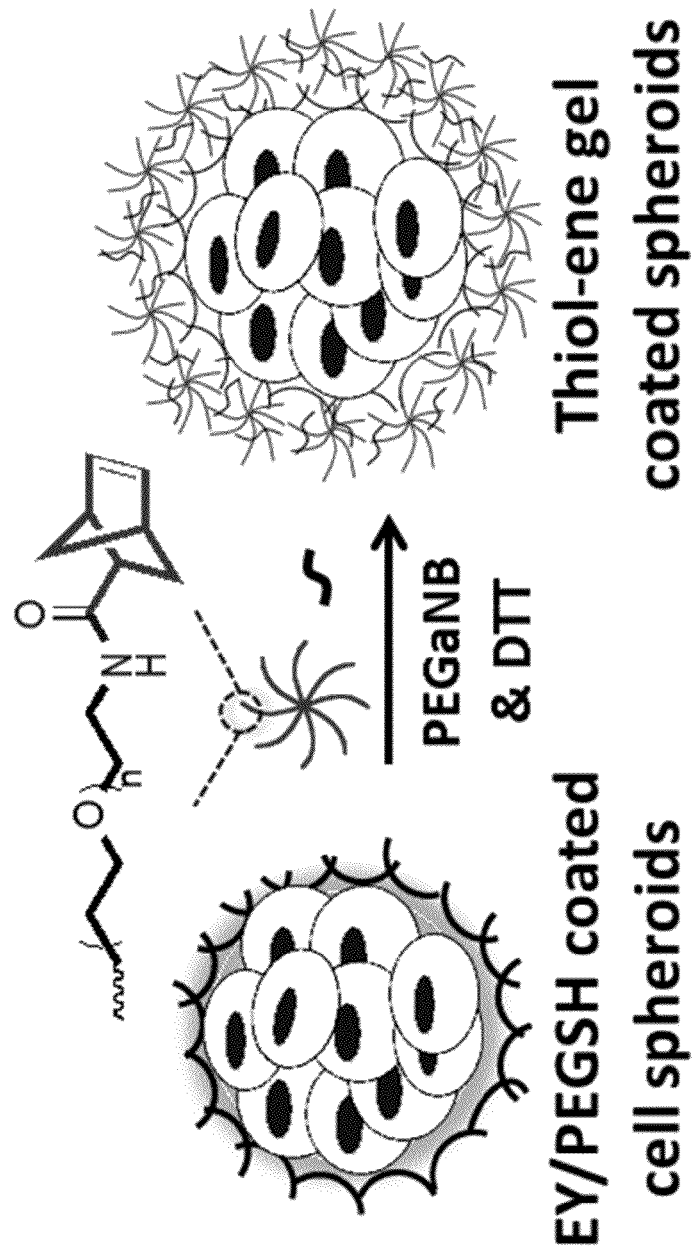
FIG. 22(a) shows the thiol-ene conformal coated MIN6 β-cell spheroids. MIN6 β-cell spheroids were stained with 10 mM Eosin-Y (EY) and 20 wt. % PEG-dithiol (PEGSH). A coating of PEGSH (due to the affinity of PEG to EY) is introduced, and the corresponding sulfhydryl groups engage in thiol-ene crosslinking near the cell surface. The stained cell aggregates were incubated in 20 wt. % PEG4NB and DTT solution and exposed to visible light for 1 min (Scale: 100 μm). The thickness of the thiol-ene conformal coating can be controlled as a function of polymerization time. Each dot in FIG. 22(b) represents the measurement of a discrete cell population aggregate, and the horizontal bar represents the average coated gel thickness.
Figure 22B:
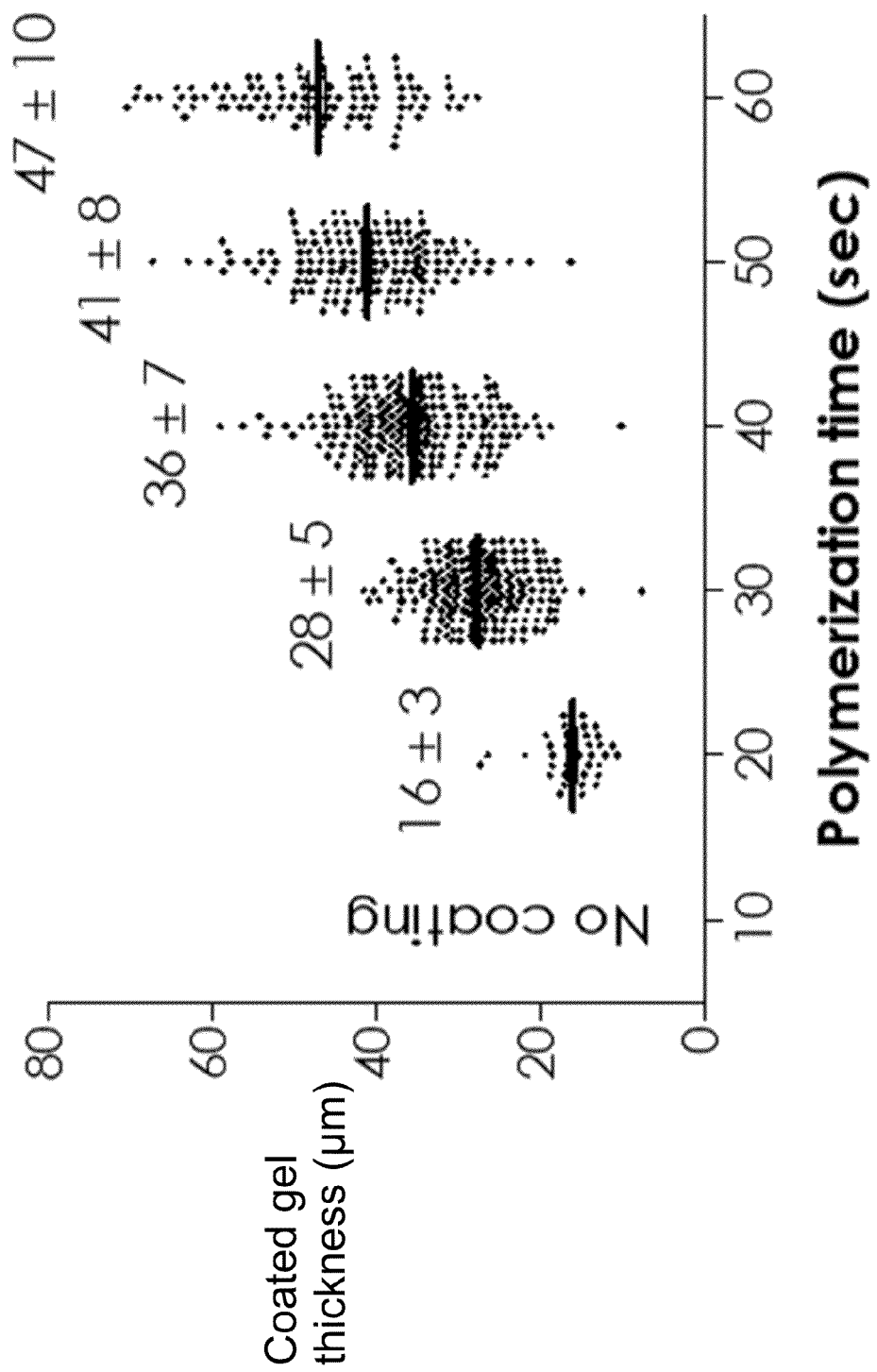

Illustratively, MIN6 β-cell spheroids or pancreatic islet cell spheroids were stained with Eosin-Y (EY) and PEG-dithiol (PEG-SH). The coating of PEGSH (due to the affinity of PEG to EY) introduced sulfhydryl groups used for thiol-ene crosslinking near the cell surface (no coating was formed when the cells were not precoated with PEGSH). PEG-norbornene macromer was used to create a non-degradable coating. FIG. 22(a) shows the results for thiol-ene conformal coated MIN6 β-cell spheroids. The thickness of the thiol-ene conformal coating is tunable, and may be controlled as a function of polymerization time, as shown in the following FIG. 22(b).

What is claimed is:

1. A composition comprising a visible light-curable mixture capable of forming a biocompatible hydrogel, the mixture comprising one or more macromers, each comprising a strained carbon-carbon multiple bond, one or more cross-linking agents, and one or more type II photoinitiators, each having at least one peak absorbance in the visible light range, wherein the mixture is free of co-initiators.

2. The composition of claim 1 wherein the peak absorbance is in the range from about 400 to about 420 nm, from about 420 to about 480 nm, from about 500 to about 530 nm, or from about 550 to about 570 nm.

3. The composition of claim 1 wherein the mixture has a rapid gel point or a rapid complete gelation time, or a combination thereof.

4. The composition of claim 1 wherein the biocompatible hydrogel exhibits low gel shear modulus or a high gel elastic modulus, or a combination thereof.

5. The composition of claim 1 wherein the mixture further comprises a therapeutic agent, a diagnostic agent, or a population of cells, or a combination thereof.

6. The composition of claim 1 wherein the biocompatible hydrogel is capable of forming a conformal gel coating for immuno-isolation of cells.

7. The composition of claim 1 wherein the photoinitiator is selected from the group consisting of eosins, Rose Bengal, riboflavins, coumarin, and 4-hydroxycoumarin, and combinations thereof.

8. The composition of claim 1 wherein the cross-linking agent is a polythiol compound.

9. The composition of claim 1 wherein the carbon-carbon multiple bond is an alkenyl group.

10. The composition of claim 1 wherein the carbon-carbon multiple bond is non-polar.

11. The composition of claim 1 wherein the carbon-carbon multiple bond is in a cyclic structure.

12. The composition of claim 1 wherein the macromer comprises a polyvalent radical where each valence is attached to a poly(ethylene glycol)-norbornenyl ester.

13. The composition of claim 1 wherein the macromer comprises a polyvalent radical where each valence is attached to a poly(ethylene glycol)-norbornenyl amide.

14. The composition of claim 12 wherein the poly(ethylene glycol) has a molecular weight in the range from about 5,000 to about 40,000.

15. A biocompatible delivery system comprising a hydrogel formed from the mixture of claim 1 and a biologically active agent wherein the biologically active agent is coated by the hydrogel.

16. The delivery system of claim 15 wherein the biologically active agent is a therapeutic agent, a diagnostic agent, or a combination thereof; a protein or nucleic acid, or combination thereof; an immunologic agent; or a population of cells; or any combination of the foregoing.

17. The delivery system of claim 15 wherein the biocompatible hydrogel is multi-layered, where each layer has independently selected characteristics.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial
<220> FEATURE:
<223> OTHER INFORMATION: bis-cysteine peptide

<400> SEQUENCE: 1

Cys Gly Gly Tyr Cys
1               5

<210> SEQ ID NO 2
<211> LENGTH: 10
<212> TYPE: PRT
<213> ORGANISM: Artificial
<220> FEATURE:
<223> OTHER INFORMATION: bis-cysteine peptide

<400> SEQUENCE: 2

Cys Gly Pro Gln Gly Ile Trp Gly Gln Cys
1               5                   10

<210> SEQ ID NO 3
<211> LENGTH: 5
<212> TYPE: PRT
<213> ORGANISM: Artificial
<220> FEATURE:
<223> OTHER INFORMATION: RGD peptide
```

```
<400> SEQUENCE: 3

Cys Arg Gly Asp Ser
1               5
```